(12) United States Patent
Barken

(10) Patent No.: US 8,409,819 B1
(45) Date of Patent: Apr. 2, 2013

(54) METHODS TO PREDICT RISK FOR CELIAC DISEASE BY DETECTING ANTI-FLAGELLIN ANTIBODY LEVELS

(75) Inventor: Derren M. Barken, San Diego, CA (US)

(73) Assignee: Nestec S.A., Vevey (CH)

( * ) Notice: Subject to any disclaimer, the term of this patent is extended or adjusted under 35 U.S.C. 154(b) by 703 days.

(21) Appl. No.: 12/392,997

(22) Filed: Feb. 25, 2009

Related U.S. Application Data

(60) Provisional application No. 61/118,968, filed on Dec. 1, 2008, provisional application No. 61/031,636, filed on Feb. 26, 2008.

(51) Int. Cl.
*G01N 33/53* (2006.01)
(52) U.S. Cl. .............................. 435/7.3; 436/63; 436/811
(58) Field of Classification Search .................... None
See application file for complete search history.

(56) References Cited

U.S. PATENT DOCUMENTS 7,361,733 B2 4/2008 Hershberg et al.
2004/0072272 A1* 4/2004 Fine .............................. 435/7.92

OTHER PUBLICATIONS

Karell et al (Human Immunology, 64:469-477, 2003).*
Targan et al, (Gastroenterology, 128:2020-28, 2005).*
Bourgey, M.; HLA related genetic risk for celiac disease; GUT 2007; 56:1054-1059.
Pietzak, M.; Stratifying Risk for Celiac Disease in a Large At-Risk United States Population by Using HLA Alleles; Clinical Gastroenterology and Hepatology; 2009; 7:966-971.
Lodes, Michael J.; Bacterial flagellin is a dominant antigen in Crohn disease; Journal of Clinical Investigation; May 2004; 1296-1306; vol. 113.

* cited by examiner

*Primary Examiner* — Patricia A Duffy
(74) *Attorney, Agent, or Firm* — Kilpatrick Townsend & Stockton LLP

(57) ABSTRACT

The present invention provides methods, assays, and kits for predicting or stratifying the risk of celiac disease (CD) based upon HLA-DQ genotype and/or anti-flagellin antibody levels. Such risk prediction or stratification can provide benefits to family members of CD patients, to a subset of patients who are being evaluated clinically for CD, and to researchers, who can utilize this strategy to establish inclusion criteria for participation in research studies investigating potential preventive interventions.

24 Claims, 2 Drawing Sheets

SEQUENCE LISTING

<160> NUMBER OF SEQ ID NOS: 2

<210> SEQ ID NO 1
<211> LENGTH: 493
<212> TYPE: PRT
<213> ORGANISM: Unknown
<220> FEATURE:
<223> OTHER INFORMATION: Description of Unknown Organism:mouse cecum uncultured bacterium
<220> FEATURE:
<223> OTHER INFORMATION: genomic DNA clone CBir-1 flagellin antigen

<400> SEQUENCE: 1

```
Met Val Val Gln His Asn Leu Gln Ala Met Asn Ser Asn Arg Met Leu
 1               5                  10                  15

Gly Ile Thr Gln Lys Thr Ala Ser Lys Ser Thr Glu Lys Leu Ser Ser
             20                  25                  30

Gly Tyr Ala Ile Asn Arg Ala Ala Asp Asn Ala Ala Gly Leu Ala Ile
         35                  40                  45

Ser Glu Lys Met Arg Lys Gln Ile Arg Gly Leu Thr Gln Ala Ser Thr
 50                  55                  60

Asn Ala Glu Asp Gly Ile Ser Ser Val Gln Thr Ala Glu Gly Ala Leu
 65                  70                  75                  80

Thr Glu Val His Asp Met Leu Gln Arg Met Asn Glu Leu Ala Ile Gln
                 85                  90                  95

Ala Ala Asn Gly Thr Asn Ser Glu Asp Asp Arg Ser Tyr Ile Gln Asp
            100                 105                 110

Glu Ile Asp Gln Leu Thr Gln Glu Ile Asp Arg Val Ala Glu Thr Thr
        115                 120                 125

Lys Phe Asn Glu Thr Tyr Leu Leu Lys Gly Asp Thr Lys Asn Val Asp
130                 135                 140

Ala Met Asp Tyr Thr Tyr Ser Tyr Lys Ala Val Thr Asn Thr Val
145                 150                 155                 160

Ala Arg Ala Ser Val Leu Ala Ala Glu Asn Thr Ala Thr Gly Met Ser
                165                 170                 175

Val Ser Ile Ser Phe Ala Ala Asn Ser Gly Lys Val Thr Ala Ala Asp
            180                 185                 190

Ser Asn Asn Leu Ala Lys Ala Ile Arg Asp Gln Gly Phe Thr Ile Thr
        195                 200                 205

Thr Ser Thr Gln Asn Gly Lys Val Val Tyr Gly Leu Glu Leu Asn Gly
    210                 215                 220

Ser Asp Ala Lys Ala Asn Tyr Thr Val Ser Thr Val Ser Met Glu Ala
225                 230                 235                 240

Gly Thr Phe Lys Ile Leu Asn Ser Asn Lys Gln Val Ala Ser Val
                245                 250                 255

Thr Ile Ser Thr Thr Ala Ser Phe Lys Lys Val Ser Gly Met Ser Gln
            260                 265                 270

Ile Val Thr Ala Tyr Ser Val Ser Ala Ala Tyr Ala Thr Gly Asp Val
        275                 280                 285

Tyr Ser Leu Tyr Asp Ala Asp Gly Asn Ala Ile Ser Ala Asn Lys Leu
    290                 295                 300

Asp Lys Tyr Phe Thr Ala Gly Gly Ala Thr Glu Ala Gly Ile Ala
305                 310                 315                 320

Thr Thr Leu Ser Ala Asn Ser Gly Val Pro Lys Val Tyr Asp Val Leu
                325                 330                 335
```

```
Gly Lys Glu Val Ser Ala Val Ser Ile Ala Ser Thr Leu Val Thr Ala
            340                 345                 350

Val Lys Asp Lys Thr Ala Ala Leu Lys Met Asn Phe His Val Gly Ala
            355                 360                 365

Asp Gly Thr Asp Asn Asn Lys Ile Lys Ile Asn Ile Glu Ala Met Thr
            370                 375                 380

Ala Lys Ser Leu Gly Val Asn Gly Leu Lys Val Ser Gly Ser Ser Gly
385                 390                 395                 400

Thr Asn Ala Thr Asn Ala Ile Glu Ile Ile Ala Gly Ala Ile Lys Lys
            405                 410                 415

Val Ser Thr Gln Arg Ser Ala Leu Gly Ala Val Gln Asn Arg Leu Glu
            420                 425                 430

His Thr Ile Asn Asn Leu Asp Asn Ile Val Glu Asn Thr Thr Ala Ala
            435                 440                 445

Glu Ser Gly Ile Arg Asp Thr Asp Met Ala Thr Glu Met Val Lys Tyr
            450                 455                 460

Ser Asn Ala Asn Ile Leu Ser Gln Ala Gly Gln Ser Met Leu Ala Gln
465                 470                 475                 480

Ser Asn Gln Ser Asn Gln Gly Val Leu Gln Leu Leu Gln
            485                 490

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence:synthetic
      six histidine tag

<400> SEQUENCE: 2

His His His His His His
1               5
```

METHODS TO PREDICT RISK FOR CELIAC DISEASE BY DETECTING ANTI-FLAGELLIN ANTIBODY LEVELS

CROSS-REFERENCES TO RELATED APPLICATIONS

The present application claims priority to U.S. Provisional Application No. 61/031,636, filed Feb. 26, 2008, and U.S. Provisional Application No. 61/118,968, filed Dec. 1, 2008, the disclosures of which are herein incorporated by reference in their entirety for all purposes.

BACKGROUND OF THE INVENTION

Celiac disease (CD) is common in both children and adults, and is characterized by abnormal small intestinal mucosa, permanent intolerance to gluten, and full recovery of clinical, biochemical, and histological findings when gluten is removed from the diet (although some patients are refractory). As a result, individuals diagnosed with CD are usually placed on a strict gluten-free diet. Small intestinal biopsy is mandatory for establishing the diagnosis of CD, but the diagnosis of CD is complicated by the fact that the disease may be silent, or may be present with atypical findings. Therefore, serological markers are used both to select patients requiring biopsy and to monitor response and adherence to a gluten-free diet.

Anti-endomysial antibodies have a sensitivity and specificity of close to 100% in the diagnosis of CD in individuals without immunoglobulin A (IgA) deficiency. Anti-tissue transglutaminase (tTG) antibodies are also highly sensitive and specific for diagnosing CD. In fact, a recent Celiac Advisory Board has recommended that assays for detecting only these two antibodies should be sufficient to diagnose CD. When serology and biopsy are inconclusive, testing for specific human leukocyte antigen (HLA) genes associated with CD may be helpful in screening for the disease. If particular polymorphisms in these genes are not present, it is unlikely that the individual will develop CD. A positive HLA test, however, does not mean that the individual has the disease, since these genes are also common in the general population.

Susceptibility to celiac disease is associated with specific human leukocyte antigen (HLA) DQ haplotypes HLA-DQ2 and HLA-DQ8 (Sollid et al., *J. Exp. Med.*, 169:345-350 (1989); Sollid et al., *Nat. Clin. Pract. Gastroenterol. Hepatol.*, 2(3):140-147 (2005); Koning, *Gastroenterology*, 129: 1294-1301 (2005)). The presence of HLA-DQ2 or HLA-DQ8 is necessary for the development of CD, but not sufficient, since these haplotypes are present in up to 30% of healthy individuals and in a much higher percentage of persons at risk for CD (Sollid et al., *J. Exp. Med.*, 169:345-350 (1989); Liu et al., *Gastroenterology*, 128(4 suppl 1):S33-S37 (2005); Margaritte-Jeannin et al., *Tissue Antigens*, 63:562-527 (2004)). Although other genes not yet identified likely play important roles in predisposing to the development of CD, confirmed CD patients carrying neither the DQ2 nor the DQ8 haplotype are extremely uncommon, and those not carrying at least half of the DQ2 haplotype are rare (Koning et al., *Best Pract. Res. Clin. Gastroenterol.*, 19(3):373-387 (2005), Karell et al., *Hum. Immunol.*, 64:469-477 (2003), Sollid et al., *Clin. Gastroenterol. Hepatol.*, 3:843-851 (2005), Babron et al., *Eur. J. Hum. Genet.*, 11:828-834 (2003)).

Unfortunately, genetic screening to ascertain susceptibility to CD has been of limited clinical utility because its scope has been restricted to excluding the diagnosis in individuals not carrying either the DQ2 or DQ8 haplotype (Hadithi et al., *Ann. Intern. Med.*, 147(5):294-302 (2007); Liu et al., *Gastroenterology*, 128(4 suppl 1):S33-S37 (2005)). This approach is very helpful to the roughly 40% of persons at risk for CD, on the basis of family history or clinical symptoms, who are found to be negative for HLA-DQ2 and HLA-DQ8, but it provides little useful information for the person at risk who does carry one or both of these haplotypes. For the full potential of HLA-DQ genotyping as a CD screening tool for persons at risk to be realized, the focus of risk determination must shift, from the haplotypes themselves to the heterodimers formed by the α and β chains that are the gene products coded by these HLA-DQ alleles (Koning, *Gastroenterology*, 129: 1294-1301 (2005); Bourgey et al., *Gut*, 56:1054-1059 (2007)) (see, FIG. 1) (adapted from Koning, 2005).

These DQ heterodimers are expressed on the cell surface of antigen-presenting cells in the lamina propria of the small intestine (Koning, *Gastroenterology*, 129:1294-1301 (2005); Koning et al., *Best Pract. Res. Clin. Gastroenterol.*, 19(3): 373-387 (2005); Sollid et al., *Nat. Clin. Pract. Gastroenterol. Hepatol.*, 2(3):140-147 (2005); Sollid et al., *Clin. Gastroenterol. Hepatol.*, 3:843-851 (2005)). The disease-associated DQ2 heterodimer, and to a much lesser extent the DQ8 heterodimer, avidly bind certain peptide fragments derived from gluten and present them to CD4 T cells (FIG. 2) (Sollid et al., *Nat. Clin. Pract. Gastroenterol. Hepatol.*, 2(3):140-147 (2005); Sollid et al., *Clin. Gastroenterol. Hepatol.*, 3:843-851 (2005); Kim et al., *Proc. Natl. Acad. Sci. USA*, 101:4175-4179 (2004); Qiao et al., *J. Immunol.*, 173:1757-1762 (2004)). This, in turn, stimulates a proliferation of T cells and cytokines, which appears to be a necessary, but not sufficient, first step in the pathogenesis of CD (Koning, *Gastroenterology* 129:1294-1301 (2005); Koning et al., *Best Pract. Res. Clin. Gastroenterol.*, 19(3):373-387 (2005)). Most importantly, the properties of DQ heterodimers formed from α and β chains coded by genes located in trans (i.e., from opposing chromosomes) are identical to those formed from α and β chains coded by genes located in cis (i.e., from the same chromosome) (Tollefsen et al., *J. Clin. Invest.*, 116:2226-2236 (2006), Koning, *Gastroenterology*, 129:1294-1301 (2005); Vader et al., *Proc. Natl. Acad. Sci. USA*, 100:12390-12395 (2003)). Thus, knowing the type and proportion of heterodimers that correspond to each genotype has the greatest potential of determining the genetic risk for CD.

Studies of CD epidemiology including both genetic and serologic data done in the U.S. (Fasano, *Gut*, 52:168-169 (2003)), as well as the majority of European studies (Dolinsek et al., *Wien Klin Wochenschr.*, 116 Suppl 2:8-12 (2004); Karell et al., *Hum. Immunol.*, 64:469-477 (2003); Karinen et al., *Scand. J. Gastroenterol.*, 41:1299-1304 (2006); Babron et al., *Eur. J. Hum. Genet.*, 11:828-834 (2003); Dube et al., *Gastroenterology*, 128(4 suppl 1):S57-S67 (2005)), have been limited to reporting the presence or absence of DQ2- or DQ8-associated haplotypes or their constituent alleles.

In view of the foregoing, what is needed in the art are methods for predicting whether an individual is at risk of developing celiac disease (CD), as well as methods that stratify the risk for celiac disease. The present invention satisfies these as well as other needs.

SUMMARY OF THE INVENTION

The present invention is based in-part on the surprising discovery that HLA-DQ genotype and/or anti-flagellin antibody levels can effectively predict or stratify patients at risk for CD (e.g., relatives of patients with biopsy-proven disease) into clinically meaningful risk groups. Such risk prediction or stratification can provide benefits to family members of CD patients, to a subset of patients who are being evaluated clinically for CD, and to researchers, who can utilize this strategy to establish inclusion criteria for participation in research studies investigating potential preventive interventions.

As such, in one aspect, the present invention provides a method for predicting whether an individual is at risk of developing CD, the method comprising:
(a) determining a human leukocyte antigen (HLA)-DQ genotype in a sample from the individual; and
(b) predicting the individual's risk of developing CD based upon the determined HLA-DQ genotype.

In one embodiment, the present invention provides a method for predicting whether an individual is at risk of developing CD, the method comprising:
(a) determining a human leukocyte antigen (HLA)-DQ genotype in a sample from the individual; and
(b) indicating that the determined HLA-DQ genotype is predictive of an extremely high risk (e.g., about 30-fold increased risk) of developing CD when the determined HLA-DQ genotype is a DQ2 homozygous genotype.

In some embodiments, the methods of the present invention for predicting whether an individual is at risk of developing CD may further or alternatively comprise one or more of the following steps:
(c) indicating that the determined HLA-DQ genotype is predictive of a very high risk (e.g., about 12-14-fold increased risk) of developing CD when the determined HLA-DQ genotype is a DQ2.2/DR5 or DQ2/DQ8 genotype;
(d) indicating that the determined HLA-DQ genotype is predictive of a high risk (e.g., about 9-fold increased risk) of developing CD when the determined HLA-DQ genotype is a DQ2.5 heterozygous or DQ8 homozygous genotype;
(e) indicating that the determined HLA-DQ genotype is predictive of an elevated risk (e.g., about 2-fold increased risk) of developing CD when the determined HLA-DQ genotype is a DQ8 heterozygous genotype;
(f) indicating that the determined HLA-DQ genotype is predictive of little to no risk of developing CD when the determined HLA-DQ genotype is a DQ2.2 heterozygous genotype other than DQ2.2/DR5; and/or
(g) indicating that the determined HLA-DQ genotype is predictive of little to no risk of developing CD when the determined HLA-DQ genotype is neither a DQ2 genotype nor a DQ8 genotype.

In a preferred embodiment, the present invention provides a method for predicting whether an individual is at risk of developing CD, the method comprising:
(a) determining a human leukocyte antigen (HLA)-DQ genotype in a sample from the individual;
(b) indicating that the determined HLA-DQ genotype is predictive of an extremely high risk of developing CD when the determined HLA-DQ genotype is a DQ2 homozygous genotype;
(c) indicating that the determined HLA-DQ genotype is predictive of a very high risk of developing CD when the determined HLA-DQ genotype is a DQ2.2/DR5 or DQ2/DQ8 genotype;
(d) indicating that the determined HLA-DQ genotype is predictive of a high risk of developing CD when the determined HLA-DQ genotype is a DQ2.5 heterozygous or DQ8 homozygous genotype;
(e) indicating that the determined HLA-DQ genotype is predictive of an elevated risk of developing CD when the determined HLA-DQ genotype is a DQ8 heterozygous genotype; and
(f) indicating that the determined HLA-DQ genotype is predictive of little to no risk of developing CD when (i) the determined HLA-DQ genotype is a DQ2.2 heterozygous genotype other than DQ2.2/DR5 or (ii) the determined HLA-DQ genotype is neither a DQ2 genotype nor a DQ8 genotype.

In another aspect, the methods herein stratify the risk for CD according to HLA-DQ genotype so as to expand the potential clinical utility of this type of genetic testing. As such, the present invention also provides a method for stratifying an individual's risk of developing CD, the method comprising:
(a) determining a human leukocyte antigen (HLA)-DQ genotype in a sample from the individual; and
(b) evaluating, identifying, or assessing the individual's risk of developing CD based upon the determined HLA-DQ genotype.

In one embodiment, the present invention provides a method for stratifying an individual's risk of developing CD, the method comprising:
(a) determining a human leukocyte antigen (HLA)-DQ genotype in a sample from the individual; and
(b) indicating that the determined HLA-DQ genotype is associated with an extremely high risk (e.g., about 30-fold increased risk) of developing CD when the determined HLA-DQ genotype is a DQ2 homozygous genotype.

In certain embodiments, the methods of the present invention for stratifying an individual's risk of developing CD may further or alternatively comprise one or more of the following steps:
(c) indicating that the determined HLA-DQ genotype is associated with a very high risk (e.g., about 12-14-fold increased risk) of developing CD when the determined HLA-DQ genotype is a DQ2.2/DR5 or DQ2/DQ8 genotype;
(d) indicating that the determined HLA-DQ genotype is associated with a high risk (e.g., about 9-fold increased risk) of developing CD when the determined HLA-DQ genotype is a DQ2.5 heterozygous or DQ8 homozygous genotype;
(e) indicating that the determined HLA-DQ genotype is associated with an elevated risk (e.g., about 2-fold increased risk) of developing CD when the determined HLA-DQ genotype is a DQ8 heterozygous genotype;
(f) indicating that the determined HLA-DQ genotype is associated with little to no risk of developing CD when the determined HLA-DQ genotype is a DQ2.2 heterozygous genotype other than DQ2.2/DR5; and/or
(g) indicating that the determined HLA-DQ genotype is associated with little to no risk of developing CD when the determined HLA-DQ genotype is neither a DQ2 genotype nor a DQ8 genotype.

In a preferred embodiment, the present invention provides a method for stratifying an individual's risk of developing CD, the method comprising:
(a) determining a human leukocyte antigen (HLA)-DQ genotype in a sample from the individual;
(b) indicating that the determined HLA-DQ genotype is associated with an extremely high risk of developing CD when the determined HLA-DQ genotype is a DQ2 homozygous genotype;

(c) indicating that the determined HLA-DQ genotype is associated with a very high risk of developing CD when the determined HLA-DQ genotype is a DQ2.2/DR5 or DQ2/DQ8 genotype;

(d) indicating that the determined HLA-DQ genotype is associated with a high risk of developing CD when the determined HLA-DQ genotype is a DQ2.5 heterozygous or DQ8 homozygous genotype;

(e) indicating that the determined HLA-DQ genotype is associated with an elevated risk of developing CD when the determined HLA-DQ genotype is a DQ8 heterozygous genotype; and (f) indicating that the determined HLA-DQ genotype is associated with little to no risk of developing CD when (i) the determined HLA-DQ genotype is a DQ2.2 heterozygous genotype other than DQ2.2/DR5 or (ii) the determined HLA-DQ genotype is neither a DQ2 genotype nor a DQ8 genotype.

In some embodiments, the HLA genotyping methods of the present invention may be useful to aid in the prediction or stratification of an individual's risk of developing CD. In other embodiments, the HLA genotyping methods of the present invention may be useful for improving the prediction or stratification of an individual's risk of developing CD.

In yet other embodiments, the HLA genotyping methods of the present invention for predicting or stratifying an individual's risk of developing CD further comprises determining the presence or level of one or more markers such as biochemical or serological markers (e.g., anti-flagellin antibodies) in the same sample or in a different sample obtained from the individual.

In addition, the methods described herein provide valuable information on the distribution of HLA-DQ genotypes in the U.S. population at risk for CD. Such information can further quantify the relationship between the expression of CD-associated heterodimers and the occurrence of CD.

In yet another aspect, the present invention provides a method for predicting whether an individual is at risk of developing CD, the method comprising:

(a) determining a level of anti-flagellin antibodies (e.g., anti-CBir-1 flagellin antibodies) in a sample from the individual; and (b) indicating that the determined level of anti-flagellin antibodies is predictive of a high risk of developing CD when the determined level of anti-flagellin antibodies is elevated in the sample relative to a control.

In a related aspect, the present invention provides a method for stratifying an individual's risk of developing CD, the method comprising:

(a) determining a level of anti-flagellin antibodies (e.g., anti-CBir-1 flagellin antibodies) in a sample from the individual; and (b) indicating that the determined level of anti-flagellin antibodies is associated with a high risk of developing CD when the determined level of anti-flagellin antibodies is elevated in the sample relative to a control.

In a further aspect, the present invention provides a method for predicting whether an individual is at risk of developing CD, the method comprising:

(a) contacting a sample from an individual (e.g., one suspected of developing CD) with a flagellin antigen (e.g., CBir-1 flagellin), or reactive fragment thereof, under conditions suitable to form a complex of the flagellin antigen, or reactive fragment thereof, and anti-flagellin antibody (e.g., anti-CBir-1 flagellin antibody);

(b) contacting the complex with a labeled antibody to form a labeled complex;

(c) detecting the level of the labeled complex with a detection device, thereby determining a level of anti-flagellin antibodies; and (d) indicating that the determined level of anti-flagellin antibodies is predictive of a high risk of developing CD when the determined level of anti-flagellin antibodies is elevated in the sample relative to a control.

In a related aspect, the present invention provides a method for stratifying an individual's risk of developing CD, the method comprising:

(a) contacting a sample from an individual (e.g., one suspected of developing CD) with a flagellin antigen (e.g., CBir-1 flagellin), or reactive fragment thereof, under conditions suitable to form a complex of the flagellin antigen, or reactive fragment thereof, and anti-flagellin antibody (e.g., anti-CBir-1 flagellin antibody);

(b) contacting the complex with a labeled antibody to form a labeled complex;

(c) detecting the level of the labeled complex with a detection device, thereby determining a level of anti-flagellin antibodies; and (d) indicating that the determined level of anti-flagellin antibodies is associated with a high risk of developing CD when the determined level of anti-flagellin antibodies is elevated in the sample relative to a control.

In certain embodiments, the methods of the present invention for predicting or stratifying an individual's risk of developing CD may further comprise the step of obtaining a sample from the individual prior to step (a). Suitable samples include, but are not limited to, whole blood, serum, saliva, plasma, urine, feces, or a tissue biopsy. In one preferred embodiment, the sample is a whole blood sample. In one preferred embodiment, the sample is saliva. In the whole blood sample embodiment, HLA-DQ genotyping may be performed on nucleic acid (e.g., DNA) isolated from the blood sample. In another preferred embodiment, the sample is a serum sample. In this embodiment, a serum sample may be contacted with a flagellin antigen, or reactive fragment thereof, under conditions suitable to form a complex of the flagellin antigen, or reactive fragment thereof, and anti-flagellin antibody. In yet another preferred embodiment, saliva is used to isolate antibodies such as anti-tissue transglutaminase (tTG) antibodies, anti-endomysial antibodies (EMA), or anti-gluten/tTG complex antibodies. Other antibodies as described herein can also be isolated.

In some embodiments, the methods of the present invention are in the form of an assay, kit, or system for predicting or stratifying an individual's risk of developing CD. In certain instances, reagents and/or instructions are provided for applying HLA-DQ genotyping analysis on a sample obtained from the individual. In certain other instances, reagents and/or instructions are provided for applying an immunoassay such as an ELISA to determine the level of anti-flagellin antibodies such as anti-CBir-1 flagellin antibodies in a sample obtained from the individual.

In certain embodiments, the present invention provides a kit for predicting whether an individual is at risk of developing CD, the kit comprising:

(a) one or more reagents for determining a human leukocyte antigen (HLA)-DQ genotype in a sample from the individual; and (b) instructions for predicting the individual's risk of developing CD based upon the determined HLA-DQ genotype.

In related embodiments, the present invention provides a kit for stratifying an individual's risk of developing CD, the kit comprising:

(a) one or more reagents for determining a human leukocyte antigen (HLA)-DQ genotype in a sample from the individual; and
(b) instructions for evaluating, identifying, or assessing the individual's risk of developing CD based upon the determined HLA-DQ genotype.

In certain other embodiments, the present invention provides a kit for predicting whether an individual is at risk of developing CD, the kit comprising:
(a) one or more reagents for determining a level of anti-flagellin antibodies (e.g., anti-CBir-1 flagellin antibodies) in a sample from the individual; and
(b) instructions for predicting the individual's risk of developing CD based upon the determined level of anti-flagellin antibodies.

In related embodiments, the present invention provides a kit for stratifying an individual's risk of developing CD, the kit comprising:
(a) one or more reagents for determining a level of anti-flagellin antibodies (e.g., anti-CBir-1 flagellin antibodies) in a sample from the individual; and
(b) instructions for evaluating, identifying, or assessing the individual's risk of developing CD based upon the determined level of anti-flagellin antibodies.

In one preferred embodiment, the kit for predicting or stratifying an individual's risk of developing CD comprises:
(a) a solid support (e.g., plate well) containing a flagellin antigen (e.g., CBir-1 flagellin), or reactive fragment thereof;
(b) a labeled antibody (e.g., anti-IgA, IgG, or IgM antibody);
(c) instructions for determining a level of anti-flagellin antibodies (e.g., anti-CBir-1 flagellin antibodies) in the individual's sample; and
(d) instructions for predicting or stratifying the individual's risk of developing CD based upon the determined level of anti-flagellin antibodies.

In some instances, the kits of the present invention may be useful to aid in the prediction of an individual's risk of developing CD. In other instances, the kits of the present invention may be useful for improving the prediction of an individual's risk of developing CD. In further instances, the kits of the present invention may be useful to aid in the stratification of an individual's risk of developing CD. In additional instances, the kits of the present invention may be useful for improving the stratification of an individual's risk of developing CD.

These and other embodiments, aspects and objects will become more apparent when read with the accompanying detailed description and figures which follow.

DETAILED DESCRIPTION OF THE INVENTION

I. Introduction

Figure 1A:
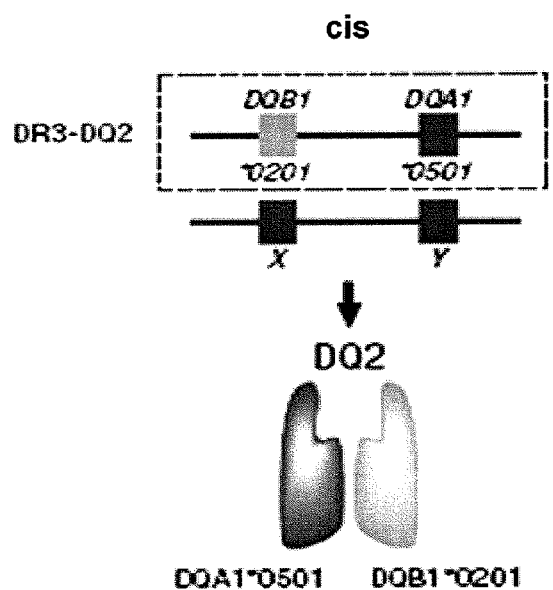
FIG. 1 illustrates heterodimer formation in cis (FIG. 1A) or trans (FIG. 1B) in relation to HLA-DQ haplotypes.
Figure 1B:
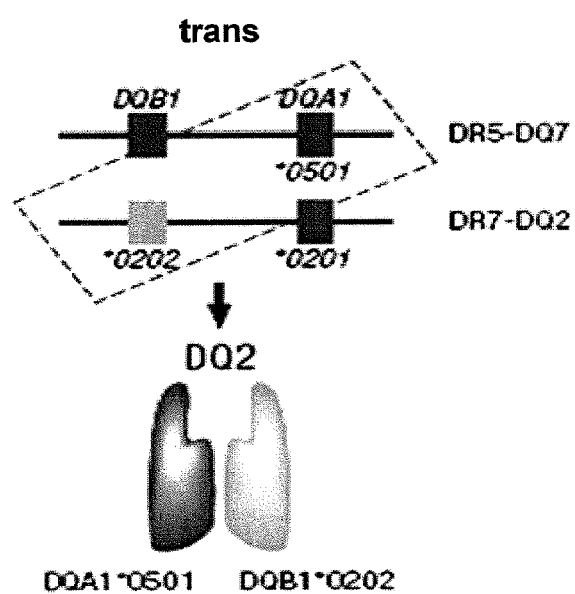
Figure 2:
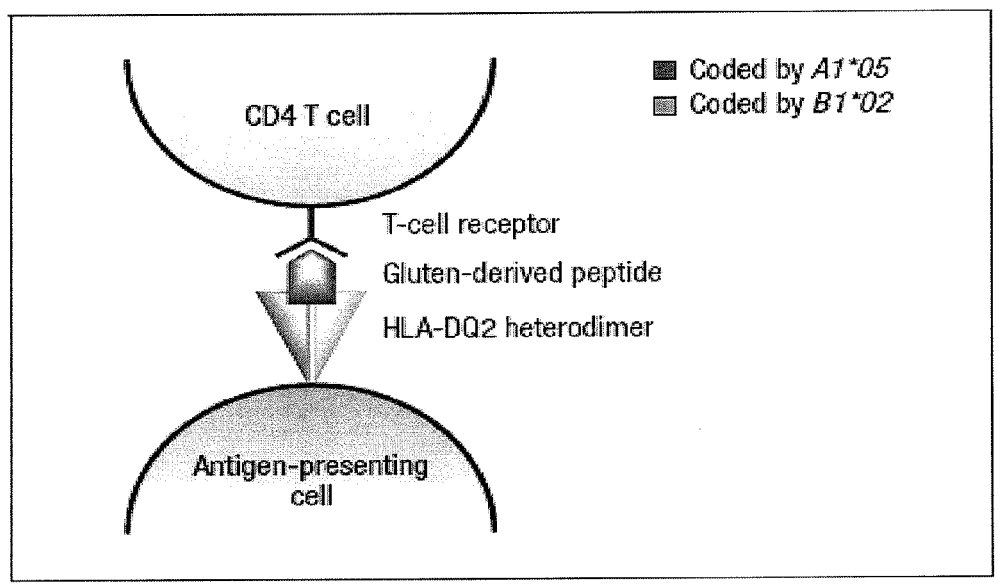
FIG. 2 illustrates antigen presentation to CD4 T cell.

Gluten is the protein part of wheat, rye, barley, triticale, millet, oat, and other related grains. Some individuals cannot tolerate gluten when it comes in contact with the small intestine. This condition is known as celiac disease (CD), which is sometimes called non-tropical sprue or gluten sensitive enteropathy. There is also evidence that dermatitis herpetiformis (DH), the skin manifestation of celiac disease, is associated with gluten intolerance. Since individuals with CD or DH suffer damage to the villi in the lamina propria and crypt regions of their small intestine when they eat specific food-grain antigens, they must follow a strict gluten-free diet.

Celiac disease is generally considered to be an autoimmune disease and the antibodies found in the serum of the patients support the theory that the disease is immunological in nature. Antibodies to tissue transglutaminase (tTGase or tTG) and gliadin appear in almost 100% of the patients with active CD, and the presence of such antibodies, particularly of the IgA class, has been used in diagnosis of the disease.

In addition, the large majority of patients express the HLA-DQ2 and/or DQ8 molecules. It is believed that intestinal damage is caused by interactions between specific gliadin oligopeptides and the HLA-DQ2 or DQ8 antigen, which in turn induce proliferation of T lymphocytes in the sub-epithelial layers. T helper 1 cells and cytokines apparently play a major role in a local inflammatory process leading to villous atrophy of the small intestine.

The present invention provides methods, assays, kits, and systems for predicting or stratifying the risk of celiac disease (CD) based upon HLA-DQ genotype and/or anti-flagellin antibody levels. In certain aspects, HLA-DQ genotyping or measuring anti-flagellin antibody levels can effectively predict or stratify patients at risk for CD (e.g., relatives of patients with biopsy-proven disease) into clinically meaningful risk groups. As such, the present invention advantageously benefits family members of CD patients, individuals who are being evaluated clinically for CD, and researchers working in this area.

II. Definitions

As used herein, the following terms have the meanings ascribed to them unless specified otherwise.

The term "celiac disease" or "CD" refers to a disorder of the intestinal mucosa that is typically associated with villous atrophy, crypt hyperplasia, and/or inflammation of the mucosal lining of the small intestine. In addition to the malabsorption of nutrients, individuals with celiac disease are at risk for mineral deficiency, vitamin deficiency, osteoporosis, autoimmune diseases, and intestinal malignancies (e.g., lymphoma and carcinoma). Without being bound by any particular theory, it is thought that exposure to proteins such as gluten (e.g., glutenin and prolamine proteins which are present in wheat, rye, barley, oats, millet, triticale, spelt, and kamut), in the appropriate genetic and environmental context, is responsible for causing celiac disease.

The term "dermatitis herpetiformis" or "DH" refers to the skin manifestation of celiac disease. Individuals with dermatitis herpetiformis typically have a chronic, extremely itchy rash consisting of papules and/or vesicles. Without being bound by any particular theory, it is thought that dermatitis herpetiformis is associated with sensitivity of the intestine to gluten in the diet.

The term "sample" includes any biological specimen obtained from an individual. Suitable samples for use in the present invention include, without limitation, whole blood, plasma, serum, saliva, urine, stool (i.e., feces), tears, any other bodily fluid, tissue samples (e.g., biopsy), and cellular extracts thereof (e.g., red blood cellular extract). In one preferred embodiment, the sample is a whole blood sample. In another preferred embodiment, the sample is a serum sample. The use of samples such as serum, saliva, and urine is well known in the art (see, e.g., Hashida et al., *Clin. Lab. Anal.*, 11:267-86 (1997)). One skilled in the art will appreciate that nucleic acid may be isolated from samples such as whole blood prior to HLA-DQ genotyping. One skilled in the art will also appreciate that samples such as serum can be diluted prior to the analysis of antibody (e.g., anti-flagellin antibody) or HLA levels.

The term "individual," "subject," or "patient" typically refers to humans, but also to other animals including, e.g., other primates, rodents, canines, felines, equines, ovines, porcines, and the like.

The term "gene" refers to the segment of DNA involved in producing a polypeptide chain; it includes regions preceding and following the coding region, such as the promoter and 3'-untranslated region, respectively, as well as intervening sequences (introns) between individual coding segments (exons).

The term "genotype" refers to the genetic composition of an organism, including, for example, whether a diploid organism is heterozygous or homozygous for one or more variant alleles of interest.

The term "polymorphism" refers to the occurrence of two or more genetically determined alternative sequences or alleles in a population. A "polymorphic site" refers to the locus at which divergence occurs. Preferred polymorphic sites have at least two alleles, each occurring at a particular frequency in a population. A polymorphic locus may be as small as one base pair (i.e., single nucleotide polymorphism or SNP). Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allele is arbitrarily designated as the reference allele, and other alleles are designated as alternative alleles, "variant alleles," or "variances." The allele occurring most frequently in a selected population is sometimes referred to as the "wild-type" allele. Diploid organisms may be homozygous or heterozygous for the variant alleles. The variant allele may or may not produce an observable physical or biochemical characteristic ("phenotype") in an individual carrying the variant allele. For example, a variant allele may alter the enzymatic activity of a protein encoded by a gene of interest.

III. Description of the Embodiments

The present invention provides methods, assays, kits, and systems for predicting or stratifying the risk of celiac disease (CD) based upon HLA-DQ genotype and/or anti-flagellin antibody levels. In certain aspects, the methods, assays, kits, and systems of the present invention find utility in aiding in the prediction or stratification of an individual's risk of developing CD. In certain other aspects, the methods, assays, kits, and systems of the present invention find utility in improving the prediction or stratification of an individual's risk of developing CD.

In one aspect, the present invention provides a method for predicting whether an individual is at risk of developing CD, the method comprising:
(a) determining a human leukocyte antigen (HLA)-DQ genotype in a sample from the individual; and
(b) predicting the individual's risk of developing CD based upon the determined HLA-DQ genotype.

In one embodiment, the present invention provides a method for predicting whether an individual is at risk of developing CD, the method comprising:
(a) determining a human leukocyte antigen (HLA)-DQ genotype in a sample from the individual; and
(b) indicating that the determined HLA-DQ genotype is predictive of an extremely high risk (e.g., about 30-fold increased risk) of developing CD when the determined HLA-DQ genotype is a DQ2 homozygous genotype.

In some embodiments, the methods of the present invention for predicting whether an individual is at risk of developing CD may further or alternatively comprise one or more of the following steps:
(c) indicating that the determined HLA-DQ genotype is predictive of a very high risk (e.g., about 12-14-fold increased risk) of developing CD when the determined HLA-DQ genotype is a DQ2.2/DR5 or DQ2/DQ8 genotype;
(d) indicating that the determined HLA-DQ genotype is predictive of a high risk (e.g., about 9-fold increased risk) of developing CD when the determined HLA-DQ genotype is a DQ2.5 heterozygous or DQ8 homozygous genotype;
(e) indicating that the determined HLA-DQ genotype is predictive of an elevated risk (e.g., about 2-fold increased risk) of developing CD when the determined HLA-DQ genotype is a DQ8 heterozygous genotype;
(f) indicating that the determined HLA-DQ genotype is predictive of little to no risk of developing CD when the determined HLA-DQ genotype is a DQ2.2 heterozygous genotype other than DQ2.2/DR5; and/or
(g) indicating that the determined HLA-DQ genotype is predictive of little to no risk of developing CD when the determined HLA-DQ genotype is neither a DQ2 genotype nor a DQ8 genotype.

In a preferred embodiment, the present invention provides a method for predicting whether an individual is at risk of developing CD, the method comprising:
(a) determining a human leukocyte antigen (HLA)-DQ genotype in a sample from the individual;
(b) indicating that the determined HLA-DQ genotype is predictive of an extremely high risk of developing CD when the determined HLA-DQ genotype is a DQ2 homozygous genotype;
(c) indicating that the determined HLA-DQ genotype is predictive of a very high risk of developing CD when the determined HLA-DQ genotype is a DQ2.2/DR5 or DQ2/DQ8 genotype;
(d) indicating that the determined HLA-DQ genotype is predictive of a high risk of developing CD when the determined HLA-DQ genotype is a DQ2.5 heterozygous or DQ8 homozygous genotype;
(e) indicating that the determined HLA-DQ genotype is predictive of an elevated risk of developing CD when the determined HLA-DQ genotype is a DQ8 heterozygous genotype; and
(f) indicating that the determined HLA-DQ genotype is predictive of little to no risk of developing CD when (i) the determined HLA-DQ genotype is a DQ2.2 heterozygous genotype other than DQ2.2/DR5 or (ii) the determined HLA-DQ genotype is neither a DQ2 genotype nor a DQ8 genotype.

In another aspect, the methods herein stratify the risk for CD according to HLA-DQ genotype so as to expand the potential clinical utility of this type of genetic testing. As such, the present invention also provides a method for stratifying an individual's risk of developing CD, the method comprising:
(a) determining a human leukocyte antigen (HLA)-DQ genotype in a sample from the individual; and (b) evaluating, identifying, or assessing the individual's risk of developing CD based upon the determined HLA-DQ genotype.

In one embodiment, the present invention provides a method for stratifying an individual's risk of developing CD, the method comprising:
(a) determining a human leukocyte antigen (HLA)-DQ genotype in a sample from the individual; and
(b) indicating that the determined HLA-DQ genotype is associated with an extremely high risk (e.g., about 30-fold increased risk) of developing CD when the determined HLA-DQ genotype is a DQ2 homozygous genotype.

In certain embodiments, the methods of the present invention for stratifying an individual's risk of developing CD may further or alternatively comprise one or more of the following steps:
(c) indicating that the determined HLA-DQ genotype is associated with a very high risk (e.g., about 12-14-fold increased risk) of developing CD when the determined HLA-DQ genotype is a DQ2.2/DR5 or DQ2/DQ8 genotype;
(d) indicating that the determined HLA-DQ genotype is associated with a high risk (e.g., about 9-fold increased risk) of developing CD when the determined HLA-DQ genotype is a DQ2.5 heterozygous or DQ8 homozygous genotype;
(e) indicating that the determined HLA-DQ genotype is associated with an elevated risk (e.g., about 2-fold increased risk) of developing CD when the determined HLA-DQ genotype is a DQ8 heterozygous genotype;
(f) indicating that the determined HLA-DQ genotype is associated with little to no risk of developing CD when the determined HLA-DQ genotype is a DQ2.2 heterozygous genotype other than DQ2.2/DR5; and/or
(g) indicating that the determined HLA-DQ genotype is associated with little to no risk of developing CD when the determined HLA-DQ genotype is neither a DQ2 genotype nor a DQ8 genotype.

In a preferred embodiment, the present invention provides a method for stratifying an individual's risk of developing CD, the method comprising:
(a) determining a human leukocyte antigen (HLA)-DQ genotype in a sample from the individual;
(b) indicating that the determined HLA-DQ genotype is associated with an extremely high risk of developing CD when the determined HLA-DQ genotype is a DQ2 homozygous genotype;
(c) indicating that the determined HLA-DQ genotype is associated with a very high risk of developing CD when the determined HLA-DQ genotype is a DQ2.2/DR5 or DQ2/DQ8 genotype;
(d) indicating that the determined HLA-DQ genotype is associated with a high risk of developing CD when the determined HLA-DQ genotype is a DQ2.5 heterozygous or DQ8 homozygous genotype;
(e) indicating that the determined HLA-DQ genotype is associated with an elevated risk of developing CD when the determined HLA-DQ genotype is a DQ8 heterozygous genotype; and
(f) indicating that the determined HLA-DQ genotype is associated with little to no risk of developing CD when (i) the determined HLA-DQ genotype is a DQ2.2 heterozygous genotype other than DQ2.2/DR5 or (ii) the determined HLA-DQ genotype is neither a DQ2 genotype nor a DQ8 genotype.

Suitable samples include, but are not limited to, whole blood, serum, plasma, urine, feces, or a tissue biopsy. In a preferred aspect, standard serologic testing is used to first assay for the presence of anti-endomysial antibody (EMA), and EMA positivity can then be used as a proxy for a diagnosis of CD.

As used herein, the term "anti-endomysial antibody (EMA)" includes an antibody that recognizes an endomysial antigen (e.g., the tTG component of smooth muscle endomysium) or a fragment thereof. One skilled in art will understand that the endomysial antigen or fragment thereof can be used in an assay, e.g., an immunoassay or immunohistochemical assay, to detect or determine the level of one or more anti-endomysial antibodies in a sample from an individual. Such endomysial antigens can be synthesized, expressed, isolated, and/or purified according to any method known in the art. Suitable ELISA kits for determining the presence or level of an EMA antibody such as an EMA IgA and/or IgG antibody in a serum or plasma sample are available, e.g., from Euroimmun AG (Lübeck, Germany) or the Binding Site Inc. A technique for determining the presence or level of an EMA antibody in a serum or plasma sample using an indirect fluorescent antibody (IFA) assay is described, e.g., in Pacht et al., Isr. J. Med. Sci., 31:218-220 (1995). Suitable IFA assay kits for the qualitative or semi-quantitative detection of an EMA antibody in a serum or plasma sample are available, e.g., from Cambridge Life Sciences Ltd. (Cambridge, United Kingdom) and Hemagen Diagnostics, Inc. (Columbia, Md.).

The determination of the presence or absence of polymorphisms at the HLA genetic locus is particularly useful in the methods of the present invention. In certain embodiments, a genotypic analysis for identifying particular alleles in the HLA-A, HLA-B, HLA-C, HLA-DP (e.g., DPA1, DPB1), HLA-DQ (e.g., DQA1, DQB1), and/or HLA-DR (e.g., DRA1, DRB1) genes can be performed on a sample from an individual. Non-limiting examples of allelic variants that can be detected using the methods of the present invention include HLA-A*01-*80, HLA-B*07-*83, HLA-Cw*01-*18, HLA-DQA1*01-*06, HLA-DQB1*02-*06, HLA-DPB1*01-*98, HLA-DRB1*01-*16, HLA-DRB3, HLA-DRB4, and/or HLA-DRB5. In preferred embodiments, the presence or absence of an HLA-DQ2 (DQA1*05/DQB1*02) and/or HLA-DQ8 (DQA1*0301/DQB1*0302) haplotype is determined in a sample from an individual. Suitable kits for determining the presence or absence of particular HLA haplotypes are available, e.g., from Innogenetics Inc. (Alpharetta, Ga.), which provides line probe assays for the molecular typing of all known HLA alleles (see also, U.S. Pat. Nos. 5,883,238 and 6,528,261); or GenoVision Inc. (West Chester, Pa.), which provides assays using PCR amplification with sequence-specific primers for the molecular typing of all known HLA alleles. In certain aspects, the presence or absence of the at least one HLA-DQ genotype is determined using polymerase chain reaction (PCR) amplification, on, for example, the DQA1 and DQB1 loci.

In certain aspects, the risk as determined in the methods of the present invention is associated with the heterodimers formed by the α and β chains that are the gene products coded by HLA-DQ alleles. Without being bound by any particular theory, it is believed that the CD-associated DQ2 heterodimer is encoded by the HLA-DQ alleles DQA1*0501, DQB1*0201, and the DQ8 heterodimer is encoded by the HLA-DQ alleles DQA1*0301, DQB1*0302. More than 90% of CD patients express the DQ2 heterodimer, whereas a much smaller number, about 10%, express the DQ8 heterodimer. DQ8 heterodimers can form from only one specific combination of α and β chains (i.e., the specific combination of alleles that comprise the HLA-DQ8 haplotype), whereas DQ2 heterodimers can be formed from one of four possible combinations of peptide chains coded by alleles found on HLA-DQ2.5 (DQA1*0501-DQB1*0201, also called the DR3 haplotype), HLA-DQ2.2 (DQA1*0201-DQB1*0202, also called the DR7 haplotype), and DR5 (DQA1*0501-DQB1*0301). The DQ2 heterodimer encoded by the alleles DQA1*05 and DQB1*02 confers an equal risk for CD regardless of which of these allelic variants is responsible for its generation.

As used herein, the DQ2 homozygous genotype is a DQ2.5/DQ2.5 or DQ2.5/DQ2.2 genotype. In certain aspects, the presence of the DQ2 homozygous genotype is associated with an about 20, 21, 22, 23, 24, 25, 26, 27, 28, 29, 30, 31, 32, 33, 34, 35, 36, 37, 38, 39, or 40-fold (or any range or fraction therein) increased risk of developing CD. Preferably, the presence of the DQ2 homozygous genotype is associated with an about 30-fold increased risk of developing CD. In certain instances, homozygosity for DQB1*0201 is associated with a more severe form of CD, younger age at diagnosis, etc., as described in, e.g., Karinen et al., *Scand. J. Gastroenterol.,* 41:1299-1304 (2006). In certain other aspects, the presence of the DQ2.2/DR5 or DQ2/DQ8 genotype is associated with an about 6, 7, 8, 9, 10, 11, 12, 13, 14, 15, 16, 17, 18, 19, or 20-fold (or any range or fraction therein) increased risk of developing CD. Preferably, the presence of the DQ2.2/DR5 or DQ2/DQ8 genotype is associated with an about 12-14-fold increased risk of developing CD.

In further aspects, the presence of the DQ2.5 heterozygous or DQ8 homozygous genotype is associated with an about 3, 4, 5, 6, 7, 8, 9, 10, 11, 12, 13, 14, 15, 16, 17, or 18-fold (or any range or fraction therein) increased risk of developing CD. Preferably, the presence of the DQ2.5 heterozygous or DQ8 homozygous genotype is associated with an about 9-fold increased risk of developing CD.

In certain instances, the presence of the DQ8 heterozygous genotype is associated with an about 1.5, 1.75, 2, 2.25, 2.5, 3, 3.5, 4, 4.5, or 5-fold (or any range or fraction therein) increased risk of developing CD. Preferably, the presence of the DQ8 heterozygous genotype is associated with an about 2-fold increased risk of developing CD. In other instances, the absence of both DQ2 and DQ8 genotypes essentially rules out CD.

Other associated risk factors include for example, where the individual (such as a child) has a relative with CD, such as a parent or sibling. In other aspects, the individual has a symptom associated with CD. Such symptoms include, for example, abdominal cramping, bloating, abdominal distention, acidosis, dehydration, diarrhea, edema, fatigue, hypotension, anemia, muscle cramping, weight loss, depression, and combinations thereof.

In other embodiments, the methods include sending the results of the genotyping and the prediction or stratification to a clinician. In certain instances, the methods further include recommending a course of therapy to an individual predicted to be at risk of developing CD or stratified as having a specified risk of developing CD. Suitable therapy includes, but is not limited to, a gluten-free diet, glutenase therapy, tTG inhibitor therapy, and combinations thereof.

Analysis of the genotype of a marker such as a human leukocyte antigen (HLA) gene can be performed using techniques known in the art including, without limitation, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., *Biotechniques,* 13:626-633 (1992)), solid-phase sequencing (Zimmerman et al., *Methods Mol. Cell. Biol.,* 3:39-42 (1992)), sequencing with mass spectrometry such as matrix-assisted laser desorption/ionization time-of-flight mass spectrometry (MALDI-TOF/MS; Fu et al., *Nature Biotech.,* 16:381-384 (1998)), and sequencing by hybridization (Chee et al., *Science,* 274:610-614 (1996); Drmanac et al., *Science,* 260: 1649-1652 (1993); Drmanac et al., *Nature Biotech.,* 16:54-58 (1998)). Non-limiting examples of electrophoretic analysis include slab gel electrophoresis such as agarose or polyacrylamide gel electrophoresis, capillary electrophoresis, and denaturing gradient gel electrophoresis. Other methods for genotyping an individual at a polymorphic site in a marker include, e.g., the INVADER® assay from Third Wave Technologies, Inc., restriction fragment length polymorphism (RFLP) analysis, allele-specific oligonucleotide hybridization, a heteroduplex mobility assay, and single strand conformational polymorphism (SSCP) analysis.

In some embodiments, the HLA genotyping methods of the present invention for predicting or stratifying an individual's risk of developing CD further comprises determining the presence or level of one or more markers in the same sample or in a different sample from the individual.

A variety of markers, such as biochemical markers, serological markers, genetic markers, or other clinical or echographic characteristics, are suitable for use in the present invention for predicting or stratifying an individual's risk of developing CD. Examples of biochemical and serological markers include, but are not limited to, antibody markers such as anti-flagellin antibodies, anti-gluten antibodies, anti-tissue transglutaminase (tTG) antibodies, anti-endomysial antibodies (EMA), anti-gluten/tTG complex antibodies, anti-protamine sulfate antibodies, anti-protamine sulfate/tTG complex antibodies, anti-actin antibodies, anti-reticulin antibodies, anti-zonulin antibodies, anti-ATP synthase β chain antibodies, anti-enolase α antibodies, anti-jejunal antibodies, total IgA, and combinations thereof; and protein markers such as human leukocyte antigen (HLA), zonulin, motilin, interleukin, prolactin, soluble CD163, and combinations thereof. Any of a variety of classes (e.g., IgA, IgG, IgM, IgD, IgE) and subclasses of the antibody markers can be detected in the methods of the present invention. Examples of genetic markers include, without limitation, HLA genes such as class I MHC genes (e.g., HLA-A, HLA-B, and/or HLA-C) and class II MHC genes (e.g., HLA-DP, HLA-DQ, and/or HLA-DR), GM immunoglobulin allotypes, T-cell receptor genes (e.g., TCRα, TCRβ, TCRγ), dipeptidyl peptidase IV genes, aminopeptidase N genes, cytotoxic T lymphocyte-associated 4 (CTLA4) genes; and combinations thereof. In a preferred aspect, the methods of the present invention for predicting or stratifying an individual's risk of developing CD further comprises detecting or determining a level (e.g., measuring the concentration) of one or more antibodies against flagellin proteins such as Cbir-1 flagellin, flagellin X, flagellin A, flagellin B, and/or fragments thereof. See, below for a description of flagellin proteins suitable for use as antigens to detect the presence of level of anti-flagellin antibodies in a sample such as a serum sample. In certain instances, the marker is determined using an immunoassay or immunohistochemical assay. One skilled in the art will know of additional markers suitable for use in the methods of the present invention.

The term "anti-gluten/tTG complex antibody" includes an antibody that recognizes a complex between tTG and gluten or a fragment thereof. Such a complex can be formed by means of a covalent or a non-covalent interaction between gluten and tTG. For example, gluten can be covalently attached to all or a portion of tTG or gluten can be covalently attached to tTG at a site of deamidation. Alternatively, gluten can interact non-covalently (e.g., ionic, van der Waal, hydrophobic, hydrogen bonding, etc.) with tTG. One skilled in art will understand that a complex between any of the above-described gluten and tTG antigens can be used in an assay, e.g., an immunoassay, to detect or determine the level of one or more anti-gluten/tTG complex antibodies in a sample from an individual.

The term "human leukocyte antigen (HLA)" includes any of a variety of proteins at the cell surface that present antigens to immune cells such as T cells. One skilled in art will understand that the presence or level of one or more HLA molecules including, without limitation, HLA-A, HLA-B, HLA-C, HLA-DP (e.g., DPA1, DPB1), HLA-DQ (e.g., DQA1, DQB1), and HLA-DR (e.g., DRA1, DRB1) can be determined with an assay that uses an HLA-binding molecule such as an anti-HLA antibody, a cytosolic HLA-binding protein, an extracellular HLA-binding protein, fragments thereof, or the like.

In yet another aspect, the present invention provides a method for predicting whether an individual is at risk of developing CD, the method comprising:
(a) determining a level of anti-flagellin antibodies in a sample from the individual; and
(b) indicating that the determined level of anti-flagellin antibodies is predictive of a high risk of developing CD when the determined level of anti-flagellin antibodies is elevated in the sample relative to a control.

In a related aspect, the present invention provides a method for stratifying an individual's risk of developing CD, the method comprising:
(a) determining a level of anti-flagellin antibodies in a sample from the individual; and
(b) indicating that the determined level of anti-flagellin antibodies is associated with a high risk of developing CD when the determined level of anti-flagellin antibodies is elevated in the sample relative to a control.

Any anti-flagellin antibody present in a sample from an individual (e.g., one suspected of developing CD) may be detected in accordance with the methods of the present invention. In preferred embodiments, the level of anti-CBir-1 antibodies is determined. In other embodiments, the level of anti-flagellin X, anti-flagellin A, and/or anti-flagellin B antibodies is determined. As used herein, the term "anti-flagellin antibody" includes antibodies directed to a protein component of bacterial flagella as described in, e.g., PCT Patent Publication No. WO 03/053220 and U.S. Pat. No. 7,361,733. The term "flagellin" refers to a bacterial flagellum protein that is immunoreactive with an anti-flagellin antibody. Microbial flagellins are proteins found in bacterial flagellum that arrange themselves in a hollow cylinder to form the filament.

An "elevated" level of anti-flagellin antibodies is intended to include a detectable increase in the level of a given anti-flagellin antibody (e.g., anti-CBir-1 antibody) relative to a control. A detectable increase can be about 5%, 10%, 15%, 20%, 25%, 30%, 35%, 40%, 45%, 50%, 55%, 60%, 65%, 70%, 75%, 80%, 85%, 90%, 95%, 100%, or more higher than the level of a given anti-flagellin antibody detected in the control. An increase in the level of a given anti-flagellin antibody is typically measured using any method or technique known in the art such as an immunoassay or immunohistochemical assay. In preferred embodiments, the immunoassay is an enzyme-linked immunosorbent assay (ELISA). In certain instances, elevated anti-flagellin antibody levels (e.g., elevated anti-CBir-1 antibody levels) include a level above a reference value of about 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0, 25.0, 26.0, 27.0, 28.0, 29.0, 30.0, 31.0, 32.0, 33.0, 34.0, 35.0, 36.0, 37.0, 38.0, 39.0, or 40.0 EU/ml (or any range or fraction therein) when an ELISA is used. In preferred embodiments, an elevated level of anti-flagellin antibodies such as an elevated level of anti-CBir-1 antibodies is a level above a reference value of about 21.0 EU/ml. Non-limiting examples of suitable controls include samples that are negative for anti-endomysial antibodies (EMA) or samples with a DQ2.2 (DQA1*0201-11, 12, 13, 14, 15, 16, 17, 18, 19, 20, 21, 22, 23, 24, 25, 26, 27, 28, 29, 30, 31, 32, 33, 34, 35, 36, 37, 38, 39, or 40-fold (or any range or fraction therein) increased risk of developing CD. Preferably, the presence of an elevated level of anti-flagellin antibodies is associated with an about 9-fold increased risk of developing CD.

In certain instances, the sample from the individual has an HLA-DQ2.5 or HLA-DQ8 genotype. In certain other instances, the sample from the individual is positive for anti-endomysial antibodies.

In a further aspect, the present invention provides a method for predicting whether an individual is at risk of developing CD, the method comprising:
(a) contacting a sample from an individual (e.g., one suspected of developing CD) with a flagellin antigen, or reactive fragment thereof, under conditions suitable to form a complex of the flagellin antigen, or reactive fragment thereof, and anti-flagellin antibody;
(b) contacting the complex with a labeled antibody to form a labeled complex;
(c) detecting the level of the labeled complex with a detection device, thereby determining a level of anti-flagellin antibodies; and
(d) indicating that the determined level of anti-flagellin antibodies is predictive of a high risk of developing CD when the determined level of anti-flagellin antibodies is elevated in the sample relative to a control.

In a related aspect, the present invention provides a method for stratifying an individual's risk of developing CD, the method comprising:
(a) contacting a sample from an individual (e.g., one suspected of developing CD) with a flagellin antigen, or reactive fragment thereof, under conditions suitable to form a complex of the flagellin antigen, or reactive fragment thereof, and anti-flagellin antibody;
(b) contacting the complex with a labeled antibody to form a labeled complex;
(c) detecting the level of the labeled complex with a detection device, thereby determining a level of anti-flagellin antibodies; and
(d) indicating that the determined level of anti-flagellin antibodies is associated with a high risk of developing CD when the determined level of anti-flagellin antibodies is elevated in the sample relative to a control.

As above, any anti-flagellin antibody present in a sample from an individual may be detected in accordance with the methods of the present invention. In preferred embodiments, the level of anti-CBir-1 antibodies is determined. In other embodiments, the level of anti-flagellin X, anti-flagellin A, and/or anti-flagellin B antibodies is determined. The level of anti-flagellin antibody present in a sample from an individual can be determined using a flagellin protein or a fragment thereof such as an immunoreactive fragment thereof. Suitable flagellin antigens useful in determining anti-flagellin antibody levels in a sample include, without limitation, a flagellin protein such as Cbir-1 flagellin, flagellin X, flagellin A, flagellin B, fragments thereof, and combinations thereof, a flagellin polypeptide having substantially the same amino acid sequence as the flagellin protein, or a fragment thereof such as an immunoreactive fragment thereof. As used herein, a flagellin polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a naturally-occurring flagellin protein, with the amino acid identity determined using a sequence alignment program such as CLUSTALW. Such flagellin antigens can be prepared, e.g., by purification from bacterium such as *Helicobacter Bilis, Helicobacter mustelae, Helicobacter pylori, Butyrivibrio fibrisolvens*, and bacterium found in the cecum, by recombinant expression of a nucleic acid encoding a flagellin antigen, by synthetic means such as solution or solid phase peptide synthesis, or by using phage display.

In certain embodiments, the flagellin antigen is a CBir-1 flagellin comprising a polypeptide fragment consisting of at least about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, or more contiguous amino acids (including all intermediate lengths) of the full-length Cbir-1 flagellin sequence set forth in SEQ ID NO:1. Typically, the CBir-1 flagellin polypeptide fragment is immunologically reactive with an antibody that binds to the full-length Cbir-1 flagellin sequence and/or a T-cell that reacts with the full-length Cbir-1 flagellin sequence. In preferred embodiments, the polypeptide fragment is the amino terminal conserved region (amino acid residues 1-147) of the sequence set forth in SEQ ID NO:1. In other embodiments, the polypeptide fragment is the amino terminal conserved region plus the variable region (amino acid residues 1-418) of the sequence set forth in SEQ ID NO:1. In some instances, the CBir-1 flagellin antigen is a fusion protein consisting of a CBir-1 flagellin polypeptide fragment described herein and a tag such as a six histidine (SEQ ID NO:2) or glutathione S-transferase (GST) tag. In certain other embodiments, the CBir-1 flagellin antigen comprises the amino acid sequence of SEQ ID NO:1 or a sequence having substantial identity thereto (e.g., at least 80%, 85%, 90%, or 95% identity to SEQ ID NO:1). Exemplary flagellin amino acid and nucleic acid sequences (e.g., CBir-1 flagellin, Flagellin X, Flagellin B, etc.) are described in U.S. Pat. No. 7,361,733.

In some embodiments, the labeled antibody comprises a reporter group such as, for example, a fluorescent group, a radioactive group, a luminescent group, an enzyme, biotin, or a dye. In an alternative embodiment, the complex formed in step (a) is contacted with a non-immunoglobulin detection agent such as, for example, Protein G, Protein A, or a lectin. Such detection agents may comprise any of the reporter groups described above.

In other embodiments, the flagellin antigen is immobilized on a solid support. The solid support may be any material known to those of ordinary skill in the art to which polypeptides may be attached. For example, the solid support may be a test well in a microtiter plate or a nitrocellulose or other suitable membrane. Alternatively, the solid support may be a bead or disc, such as glass, fiberglass, latex, or a plastic material such as polystyrene or polyvinylchloride. The solid support may also be a magnetic particle, a fiber optic sensor, or a chip.

In certain preferred embodiments, the methods described herein for predicting or stratifying an individual's risk of developing CD contemplate the use of an enzyme-linked immunosorbent assay (ELISA) with a detection device such as, for example, a plate reader, a spectrophotometer, a fluorimeter, or other device, apparatus, or system suitable for detecting a complex formed between a flagellin antigen, or reactive fragment thereof, and anti-flagellin antibody.

In some embodiments, the methods of the present invention are in the form of an assay, kit, or system for predicting or stratifying an individual's risk of developing CD. In certain instances, reagents and/or instructions are provided for applying HLA-DQ genotyping analysis on a sample obtained from the individual. In certain other instances, reagents and/or instructions are provided for applying an immunoassay such as an ELISA to determine the level of anti-flagellin antibodies such as anti-CBir-1 flagellin antibodies in a sample obtained from the individual.

In certain embodiments, the present invention provides a kit for predicting whether an individual is at risk of developing CD, the kit comprising:
  (a) one or more reagents for determining a human leukocyte antigen (HLA)-DQ genotype in a sample from the individual; and
  (b) instructions for predicting the individual's risk of developing CD based upon the determined HLA-DQ genotype.

In related embodiments, the present invention provides a kit for stratifying an individual's risk of developing CD, the kit comprising:
  (a) one or more reagents for determining a human leukocyte antigen (HLA)-DQ genotype in a sample from the individual; and
  (b) instructions for evaluating, identifying, or assessing the individual's risk of developing CD based upon the determined HLA-DQ genotype.

Suitable reagents for HLA-DQ genotyping include, but are not limited to, allele-specific probes, sequence-specific primers (e.g., biotinylated primers), enzymes (e.g., DNA polymerase), buffers, thermocyclers, computers, computer software, etc.

In certain other embodiments, the present invention provides a kit for predicting whether an individual is at risk of developing CD, the kit comprising:
  (a) one or more reagents for determining a level of anti-flagellin antibodies (e.g., anti-CBir-1 flagellin antibodies) in a sample from the individual; and
  (b) instructions for predicting the individual's risk of developing CD based upon the determined level of anti-flagellin antibodies.

In related embodiments, the present invention provides a kit for stratifying an individual's risk of developing CD, the kit comprising:
  (a) one or more reagents for determining a level of anti-flagellin antibodies (e.g., anti-CBir-1 flagellin antibodies) in a sample from the individual; and
  (b) instructions for evaluating, identifying, or assessing the individual's risk of developing CD based upon the determined level of anti-flagellin antibodies.

In one preferred embodiment, the kit for predicting or stratifying an individual's risk of developing CD comprises:
  (a) a solid support (e.g., plate well) containing a flagellin antigen (e.g., CBir-1 flagellin), or reactive fragment thereof;
  (b) a labeled antibody (e.g., anti-IgA, IgG, or IgM antibody);
  (c) instructions for determining a level of anti-flagellin antibodies (e.g., anti-CBir-1 flagellin antibodies) in the individual's sample; and (d) instructions for predicting or stratifying the individual's risk of developing CD based upon the determined level of anti-flagellin antibodies.

Suitable reagents for detecting anti-flagellin antibody levels include, but are not limited to, flagellin polypeptides or fragments thereof (e.g., CBir-1 flagellin or immunoreactive fragments thereof), detection reagents comprising a reporter group (e.g., enzyme-labeled antibodies), solid supports (e.g., microtiter plate wells), buffers, detection devices (e.g., microtiter plate reader), computers, computer software, etc.

In some instances, the kits of the present invention may be useful to aid in the prediction of an individual's risk of developing CD. In other instances, the kits of the present invention may be useful for improving the prediction of an individual's risk of developing CD. In further instances, the kits of the present invention may be useful to aid in the stratification of an individual's risk of developing CD. In additional instances, the kits of the present invention may be useful for improving the stratification of an individual's risk of developing CD.

IV. Methods of Genotyping

A variety of means can be used to genotype an individual at a polymorphic site in a human leukocyte antigen (HLA) gene in the methods of the present invention in order to determine whether a sample (e.g., a nucleic acid sample) contains a specific HLA-DQ variant allele or haplotype. For example, enzymatic amplification of nucleic acid from an individual can be conveniently used to obtain nucleic acid for subsequent analysis. The presence or absence of a specific HLA-DQ variant allele or haplotype can also be determined directly from the individual's nucleic acid without enzymatic amplification. In certain preferred embodiments, an individual is genotyped at both the HLA-DQA1 and HLA-DQB1 loci.

Genotyping of nucleic acid from an individual, whether amplified or not, can be performed using any of various techniques. Useful techniques include, without limitation, polymerase chain reaction (PCR) based analysis, sequence analysis, and electrophoretic analysis, which can be used alone or in combination. As used herein, the term "nucleic acid" means a polynucleotide such as a single- or double-stranded DNA or RNA molecule including, for example, genomic DNA, cDNA and mRNA. This term encompasses nucleic acid molecules of both natural and synthetic origin as well as molecules of linear, circular, or branched configuration representing either the sense or antisense strand, or both, of a native nucleic acid molecule. It is understood that such nucleic acids can be unpurified, purified, or attached, for example, to a synthetic material such as a bead or column matrix.

Material containing nucleic acid is routinely obtained from individuals. Such material is any biological matter from which nucleic acid can be prepared. As non-limiting examples, material can be whole blood, serum, plasma, saliva, cheek swab, sputum, or other bodily fluid or tissue that contains nucleic acid. In one embodiment, a method of the present invention is practiced with whole blood, which can be obtained readily by non-invasive means and used to prepare genomic DNA. In another embodiment, genotyping involves amplification of an individual's nucleic acid using the polymerase chain reaction (PCR). Use of PCR for the amplification of nucleic acids is well known in the art (see, e.g., Mullis et al. (Eds.), *The Polymerase Chain Reaction*, Birkhäuser, Boston, (1994)). In yet another embodiment, PCR amplification is performed using one or more fluorescently labeled primers. In a further embodiment, PCR amplification is performed using one or more labeled or unlabeled primers that contain a DNA minor grove binder.

Any of a variety of different primers can be used to amplify an individual's nucleic acid by PCR. As understood by one skilled in the art, additional primers for PCR analysis can be designed based on the sequence flanking the polymorphic site(s) of interest. As a non-limiting example, a sequence primer can contain from about 15 to about 30 nucleotides of a sequence upstream or downstream of the polymorphic site of interest. Such primers generally are designed to have sufficient guanine and cytosine content to attain a high melting temperature which allows for a stable annealing step in the amplification reaction. Several computer programs, such as Primer Select, are available to aid in the design of PCR primers.

A Taqman® allelic discrimination assay available from Applied Biosystems can be useful for genotyping an individual at a polymorphic site and thereby determining the presence or absence of a particular HLA-DQ variant allele or haplotype. In a Taqman® allelic discrimination assay, a specific fluorescent dye-labeled probe for each allele is constructed. The probes contain different fluorescent reporter dyes such as FAM and VIC to differentiate amplification of each allele. In addition, each probe has a quencher dye at one end which quenches fluorescence by fluorescence resonance energy transfer. During PCR, each probe anneals specifically to complementary sequences in the nucleic acid from the individual. The 5' nuclease activity of Taq polymerase is used to cleave only probe that hybridizes to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. Those skilled in the art understand that improved specificity in allelic discrimination assays can be achieved by conjugating a DNA minor grove binder (MGB) group to a DNA probe as described, e.g., in Kutyavin et al., *Nuc. Acids Research* 28:655-661 (2000). Minor grove binders include, but are not limited to, compounds such as dihydrocyclopyrroloindole tripeptide (DPI3).

Sequence analysis can also be useful for genotyping an individual according to the methods described herein. In certain instances, a variant allele or haplotype of interest can be detected by sequence analysis using the appropriate primers, which are designed based on the sequence flanking the polymorphic site of interest, as is known by those skilled in the art. As a non-limiting example, a sequence primer can contain from about 15 to about 30 nucleotides of a sequence that corresponds to a sequence about 40 to about 400 base pairs upstream or downstream of the polymorphic site of interest. Such primers are generally designed to have sufficient guanine and cytosine content to attain a high melting temperature which allows for a stable annealing step in the sequencing reaction.

The term "sequence analysis" means any manual or automated process by which the order of nucleotides in a nucleic acid is determined. As an example, sequence analysis can be used to determine the nucleotide sequence of a sample of DNA. The term sequence analysis encompasses, without limitation, chemical and enzymatic methods such as dideoxy enzymatic methods including, for example, Maxam-Gilbert and Sanger sequencing as well as variations thereof. The term sequence analysis further encompasses, but is not limited to, capillary array DNA sequencing, which relies on capillary electrophoresis and laser-induced fluorescence detection and can be performed using instruments such as the MegaBACE 1000 or ABI 3700. As additional non-limiting examples, the term sequence analysis encompasses thermal cycle sequencing (see, Sears et al., *Biotechniques* 13:626-633 (1992)); solid-phase sequencing (see, Zimmerman et al., *Methods Mol. Cell. Biol.* 3:39-42 (1992); and sequencing with mass spectrometry, such as matrix-assisted laser desorption/ionization time-of-flight mass spectrometry (see, MALDI-TOF MS; Fu et al., *Nature Biotech.* 16:381-384 (1998)). The term sequence analysis further includes, but is not limited to, sequencing by hybridization (SBH), which relies on an array of all possible short oligonucleotides to identify a segment of sequence (see, Chee et al., *Science* 274:610-614 (1996); Drmanac et al., *Science* 260:1649-1652 (1993); and Drmanac et al., *Nature Biotech.* 16:54-58 (1998)). One skilled in the art understands that these and additional variations are encompassed by the term sequence analysis as defined herein.

Electrophoretic analysis also can be useful in genotyping an individual according to the methods of the present invention. "Electrophoretic analysis" as used herein in reference to one or more nucleic acids such as amplified fragments means a process whereby charged molecules are moved through a stationary medium under the influence of an electric field. Electrophoretic migration separates nucleic acids primarily on the basis of their charge, which is in proportion to their size, with smaller molecules migrating more quickly. The term electrophoretic analysis includes, without limitation, analysis using slab gel electrophoresis, such as agarose or polyacrylamide gel electrophoresis, or capillary electrophoresis. Capillary electrophoretic analysis generally occurs inside a small-diameter (50-100 m) quartz capillary in the presence of high (kilovolt-level) separating voltages with separation times of a few minutes. Using capillary electrophoretic analysis, nucleic acids are conveniently detected by UV absorption or fluorescent labeling, and single-base resolution can be obtained on fragments up to several hundred base pairs. Such methods of electrophoretic analysis, and variations thereof, are well known in the art, as described, for example, in Ausubel et al., *Current Protocols in Molecular Biology* Chapter 2 (Supplement 45) John Wiley & Sons, Inc. New York (1999).

Restriction fragment length polymorphism (RFLP) analysis can also be useful for genotyping an individual according to the methods of the present invention (see, Jarcho et al. in Dracopoli et al., *Current Protocols in Human Genetics pages* 2.7.1-2.7.5, John Wiley & Sons, New York; Innis et al., (Ed.), *PCR Protocols*, San Diego: Academic Press, Inc. (1990)). As used herein, "restriction fragment length polymorphism analysis" includes any method for distinguishing polymorphic alleles using a restriction enzyme, which is an endonuclease that catalyzes degradation of nucleic acid following recognition of a specific base sequence, generally a palindrome or inverted repeat. One skilled in the art understands that the use of RFLP analysis depends upon an enzyme that can differentiate a variant allele from a wild-type or other allele at a polymorphic site.

In addition, allele-specific oligonucleotide hybridization can be useful for genotyping an individual in the methods of the present invention. Allele-specific oligonucleotide hybridization is based on the use of a labeled oligonucleotide probe having a sequence perfectly complementary, for example, to the sequence encompassing the variant allele. Under appropriate conditions, the variant allele-specific probe hybridizes to a nucleic acid containing the variant allele but does not hybridize to the one or more other alleles, which have one or more nucleotide mismatches as compared to the probe. If desired, a second allele-specific oligonucleotide probe that matches an alternate (e.g., wild-type) allele can also be used. Similarly, the technique of allele-specific oligonucleotide amplification can be used to selectively amplify, for example, a variant allele by using an allele-specific oligonucleotide primer that is perfectly complementary to the nucleotide sequence of the variant allele but which has one or more mismatches as compared to other alleles (Mullis et al., supra). One skilled in the art understands that the one or more nucleotide mismatches that distinguish between the variant allele and other alleles are often located in the center of an allele-specific oligonucleotide primer to be used in the allele-specific oligonucleotide hybridization. In contrast, an allele-specific oligonucleotide primer to be used in PCR amplification generally contains the one or more nucleotide mismatches that distinguish between the variant and other alleles at the 3' end of the primer.

A heteroduplex mobility assay (HMA) is another well-known assay that can be used for genotyping in the methods of the present invention. HMA is useful for detecting the presence of a variant allele since a DNA duplex carrying a mismatch has reduced mobility in a polyacrylamide gel compared to the mobility of a perfectly base-paired duplex (see, Delwart et al., *Science*, 262:1257-1261 (1993); White et al., *Genomics,* 12:301-306 (1992)).

The technique of single strand conformational polymorphism (SSCP) can also be useful for genotyping in the methods of the present invention (see, Hayashi, *Methods Applic.*, 1:34-38 (1991)). This technique is used to detect variant alleles based on differences in the secondary structure of single-stranded DNA that produce an altered electrophoretic mobility upon non-denaturing gel electrophoresis. Variant alleles are detected by comparison of the electrophoretic pattern of the test fragment to corresponding standard fragments containing known alleles.

Denaturing gradient gel electrophoresis (DGGE) can be useful in the methods of the present invention. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (see, Sheffield et al., "Identifying DNA Polymorphisms by Denaturing Gradient Gel Electrophoresis" in Innis et al., supra, 1990).

In certain preferred embodiments, the presence or absence of a particular HLA variant allele or haplotype is determined using line probe assays available from Innogenetics Inc. (Alpharetta, Ga.). See, U.S. Pat. Nos. 5,883,238 and 6,528,261 for a description of embodiments directed to such line probe assays. HLA molecular genotyping assays using PCR amplification with sequence-specific primers available from Geno-Vision Inc. (West Chester, Pa.) are also suitable for use in the present invention.

Other molecular methods useful for genotyping an individual are known in the art and useful in the methods of the present invention. Such well-known genotyping approaches include, without limitation, automated sequencing and RNase mismatch techniques (see, Winter et al., *Proc. Natl. Acad. Sci.*, 82:7575-7579 (1985)). Furthermore, one skilled in the art understands that, where the presence or absence of multiple variant alleles is to be determined, individual variant alleles can be detected by any combination of molecular methods. See, in general, Birren et al. (Eds.) *Genome Analysis: A Laboratory Manual* Volume 1 (Analyzing DNA) New York, Cold Spring Harbor Laboratory Press (1997). In addition, one skilled in the art understands that multiple variant alleles can be detected in individual reactions or in a single reaction (a "multiplex" assay).

In view of the above, one skilled in the art realizes that the methods of the present invention for predicting or stratifying an individual's risk of developing CD by genotyping at a polymorphic site in an HLA gene (e.g., determining the presence or absence of particular variant alleles or haplotypes at the HLA-DQA and HLA-DQB loci) can be practiced using one or any combination of the well-known assays described above or other assays known in the art.

V. Assays

Any of a variety of assays, techniques, and kits known in the art can be used to determine the presence (or absence) or level of one or more markers in a sample to predict or stratify an individual's risk of developing CD in accordance with the present invention.

In certain aspects, the present invention relies on determining the presence or absence of at least one marker in a sample obtained from an individual. As used herein, the term "determining the presence or absence" of at least one marker includes determining the presence or absence of each marker of interest by using any quantitative or qualitative assay known to one of skill in the art. In certain instances, qualitative assays that determine the presence or absence of a particular trait, variable, or biochemical or serological substance (e.g., protein or antibody) are suitable for detecting each marker of interest. In certain other instances, quantitative assays that determine the presence or absence of RNA, protein, antibody, or activity are suitable for detecting each marker of interest.

The present invention may also rely on determining a level of at least one marker in a sample obtained from an individual. As used herein, the term "determining a level" of at least one marker includes determining the level of each marker of interest by using any direct or indirect quantitative assay known to one of skill in the art. In certain instances, quantitative assays that determine, for example, the relative or absolute amount of RNA, protein, antibody, or activity are suitable for determining the level of each marker of interest. One skilled in the art will appreciate that any assay useful for determining the level of a marker is also useful for determining the presence or absence of the marker.

As used herein, the term "antibody" includes a population of immunoglobulin molecules, which can be polyclonal or monoclonal and of any isotype, or an immunologically active fragment of an immunoglobulin molecule. Such an immunologically active fragment contains the heavy and light chain variable regions, which make up the portion of the antibody molecule that specifically binds an antigen. For example, an immunologically active fragment of an immunoglobulin molecule known in the art as Fab, Fab', or F(ab')$_2$ is included within the meaning of the term antibody.

Flow cytometry can be used to determine the presence or level of one or more markers in a sample. Such flow cytometric assays, including bead based immunoassays, can be used to determine, e.g., antibody marker levels in the same manner as described for detecting serum antibodies to *Candida albicans* and HIV proteins (see, e.g., Bishop et al., *J. Immunol. Methods*, 210:79-87 (1997); McHugh et al., *J. Immunol. Methods*, 116:213 (1989); Scillian et al., *Blood*, 73:2041 (1989)).

Phage display technology for expressing a recombinant antigen specific for a marker can also be used to determine the presence or level of one or more markers in a sample. Phage particles expressing an antigen specific for, e.g., an antibody marker can be anchored, if desired, to a multi-well plate using an antibody such as an anti-phage monoclonal antibody (Felici et al., "Phage-Displayed Peptides as Tools for Characterization of Human Sera" in Abelson (Ed.), *Methods in Enzymol.*, 267, San Diego: Academic Press, Inc. (1996)).

A variety of immunoassay techniques, including competitive and non-competitive immunoassays, can be used to determine the presence or level of one or more markers in a sample (see, e.g., Self et al., *Curr. Opin. Biotechnol.*, 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), antigen capture ELISA, sandwich ELISA, IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence (see, e.g., Schmalzing et al., *Electrophoresis*, 18:2184-2193 (1997); Bao, *J. Chromatogr. B. Biomed. Sci.*, 699:463-480 (1997)). Liposome immunoassays, such as flow-injection liposome immunoassays and liposome immunosensors, are also suitable for use in the present invention (see, e.g., Rongen et al., *J. Immunol. Methods*, 204:105-133 (1997)). In addition, nephelometry assays, in which the formation of protein/antibody complexes results in increased light scatter that is converted to a peak rate signal as a function of the marker concentration, are suitable for use in the present invention. Nephelometry assays are commercially available from Beckman Coulter (Brea, Calif.; Kit #449430) and can be performed using a Behring Nephelometer Analyzer (Fink et al., *J. Clin. Chem. Clin. Biol. Chem.*, 27:261-276 (1989)).

Antigen capture ELISA can be useful for determining the presence or level of one or more markers in a sample. For example, in an antigen capture ELISA, an antibody directed to a marker of interest is bound to a solid phase and sample is added such that the marker is bound by the antibody. The marker and antibody binding is a transformation to make a complex. After unbound proteins are removed by washing, the amount of bound marker can be quantitated using, e.g., a radioimmunoassay (see, e.g., Harlow and Lane, Antibodies: A Laboratory Manual, Cold Spring Harbor Laboratory, New York, 1988)). Sandwich ELISA can also be suitable for use in the present invention. For example, in a two-antibody sandwich assay, a first antibody is bound to a solid support, and the marker of interest is allowed to bind to the first antibody. The amount of the marker is quantitated by measuring the amount of a second antibody that binds the marker, which is transformed to make a sandwich complex. The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

A radioimmunoassay using, for example, an iodine-125 ($^{125}$I) labeled secondary antibody (Harlow and Lane, supra) is also suitable for determining the presence or level of one or more markers in a sample. A secondary antibody labeled with a chemiluminescent marker can also be suitable for use in the present invention. A chemiluminescence assay using a chemiluminescent secondary antibody is suitable for sensitive, non-radioactive detection of marker levels. Such secondary antibodies can be obtained commercially from various sources, e.g., Amersham Lifesciences, Inc. (Arlington Heights, Ill.).

The immunoassays described above are particularly useful for determining the presence or level of one or more markers in a sample. As a non-limiting example, an ELISA using a flagellin protein or a fragment thereof is useful for determining whether a sample is positive or negative for anti-flagellin antibodies, or for determining anti-flagellin antibody levels in a sample. Similarly, an ELISA using tissue transglutaminase (tTG) protein or a fragment thereof is useful for determining whether a sample is positive or negative for anti-tTG antibodies, or for determining anti-tTG antibody levels in a sample. Likewise, an ELISA using an endomysial antigen or a fragment thereof is useful for determining whether a sample is positive or negative for anti-endomysial antibodies (EMA), or for determining EMA levels in a sample. In addition, the immunoassays described above can be useful for determining the presence or level of other markers in a sample.

Specific immunological binding of the antibody to the marker of interest can be detected directly or indirectly. Direct labels include fluorescent or luminescent tags, metals, dyes, radionuclides, and the like, attached to the antibody. An antibody labeled with iodine-125 ($^{125}$I) can be used for determining the levels of one or more markers in a sample. A chemiluminescence assay using a chemiluminescent antibody specific for the marker is suitable for sensitive, non-radioactive detection of marker levels. An antibody labeled with a fluorochrome is also suitable for determining the levels of one or more markers in a sample. Examples of fluorochromes include, without limitation, DAPI, fluorescein, Hoechst 33258, R-phycocyanin, B-phycoerythrin, R-phycoerythrin, rhodamine, Texas red, and lissamine. Secondary antibodies linked to fluorochromes can be obtained commercially, e.g., goat F(ab')$_2$ anti-human IgG-FITC is available from Tago Immunologicals (Burlingame, Calif.).

Indirect labels include various enzymes well-known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which transforms the substrate to yield a soluble product readily detectable at 405 nm. Similarly, a β-galactosidase detection system can be used with the chromogenic substrate o-nitrophenyl-β-D-galactopyranoside (ONPG), which transforms the substrate to yield a soluble product detectable at 410 nm. An urease detection system can be used with a substrate such as urea-bromocresol purple (Sigma Immunochemicals; St. Louis, Mo.) to transform the substrate to yield a detectable product. A useful secondary antibody linked to an enzyme can be obtained from a number of commercial sources, e.g., goat F(ab')$_2$ anti-human IgG-alkaline phosphatase can be purchased from Jackson ImmunoResearch (West Grove, Pa.).

A signal from the direct or indirect label can be analyzed or measure by a machine or detection device, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis of the amount of marker levels can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

In certain of the above instances, the ELISA techniques described involve a transformation in order to observe a signal. For example, if an antigen is immobilized on a surface and then a specific antibody (e.g., anti-CBir-1 antibody) is washed over the surface so that it can bind to the antigen the binding event is a transformation of the antigen and antibody into an antigen-antibody complex.

Again, in certain instances, the antibody is linked to an enzyme (horseradish peroxidase (HRP), alkaline phosphatase (AP), β-galactosidase, urease, and the like) and an enzyme substrate is added so that the enzyme can transform the substrate into a product. The enzyme product can be used to generate a detectable signal. Thus, in the case of fluorescence ELISA, when light of the appropriate wavelength is shone upon the sample, any antigen/antibody complexes will fluoresce so that the amount of antigen or antibody in the sample can be inferred through the magnitude of the fluorescence. A horseradish-peroxidase detection system can be used, for example, with the chromogenic substrate tetramethylbenzidine (TMB), which transforms the TMB to a soluble product in the presence of hydrogen peroxide that is detectable at 450 nm.

In addition, the ELISA techniques herein also involve the use of a machine or detection device. The detection device can be a plate reader, a spectrophotometer, a fluorometer, a scintillation counter or some other device suitable for use in detecting the transformation of the antigen and antibody into an antigen-antibody complex.

Quantitative western blotting can also be used to detect or determine the presence or level of one or more markers in a sample. Western blots can be quantitated by well-known methods such as scanning densitometry or phosphorimaging. As a non-limiting example, protein samples are electrophoresed on 10% SDS-PAGE Laemmli gels. Primary murine monoclonal antibodies are reacted with the blot, and antibody binding can be confirmed to be linear using a preliminary slot blot experiment. Goat anti-mouse horseradish peroxidase-coupled antibodies (BioRad) are used as the secondary antibody, and signal detection performed using chemiluminescence, for example, with the Renaissance chemiluminescence kit (New England Nuclear; Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, for example, in Parra et al., *J. Vasc. Surg.*, 28:669-675 (1998).

Alternatively, a variety of immunohistochemical assay techniques can be used to determine the presence or level of one or more markers in a sample. As used herein, the term "immunohistochemical assay" encompasses techniques that utilize the visual detection of fluorescent dyes or enzymes coupled (i.e., conjugated) to antibodies that react with the marker of interest using fluorescent microscopy or light microscopy and includes, without limitation, direct fluorescent antibody assay, indirect fluorescent antibody (IFA) assay, anticomplement immunofluorescence, avidin-biotin immunofluorescence, and immunoperoxidase assays. An IFA assay, for example, can be useful for determining whether a sample is positive or negative for EMA, or for determining EMA levels in a sample. The concentration of EMA in a sample can be quantitated, e.g., through endpoint titration or through measuring the visual intensity of fluorescence compared to a known reference standard.

Alternatively, the presence or level of a marker of interest can be determined by detecting or quantifying the amount of the purified marker. Purification of the marker can be achieved, for example, by high pressure liquid chromatography (HPLC), alone or in combination with mass spectrometry (e.g., MALDI/MS, MALDI-TOF/MS, tandem MS, etc.). Qualitative or quantitative detection of a marker of interest can also be determined by well-known methods including, without limitation, Bradford assays, Coomassie blue staining, silver staining, assays for radiolabeled protein, and mass spectrometry.

The analysis of a plurality of markers may be carried out separately or simultaneously with one test sample. For separate or sequential assay of markers, suitable apparatuses include clinical laboratory analyzers such as the ElecSys (Roche), the AxSym (Abbott), the Access (Beckman), the ADVIA®, the CENTAUR® (Bayer), and the NICHOLS ADVANTAGE® (Nichols Institute) immunoassay systems. Preferred apparatuses or protein chips perform simultaneous assays of a plurality of markers on a single surface. Particularly useful physical formats comprise surfaces having a plurality of discrete, addressable locations for the detection of a plurality of different markers. Such formats include, for example, protein microarrays, or "protein chips" (see, e.g., Ng et al., *J. Cell Mol. Med.,* 6:329-340 (2002)), and certain capillary devices (see, e.g., U.S. Pat. No. 6,019,944). In these embodiments, each discrete surface location may comprise antibodies and/or antigens to immobilize one or more markers for detection at each location. Surfaces may alternatively comprise one or more discrete particles (e.g., microparticles or nanoparticles) immobilized at discrete locations of a surface, where the microparticles comprise antibodies and/or antigens to immobilize one or more markers for detection.

In addition to the above-described assays for determining the presence or level of various markers of interest, analysis of marker mRNA levels using routine techniques such as Northern analysis, reverse-transcriptase polymerase chain reaction (RT-PCR), or any other methods based on hybridization to a nucleic acid sequence that is complementary to a portion of the marker coding sequence (e.g., slot blot hybridization) are also within the scope of the present invention. Applicable PCR amplification techniques are described in, e.g., Ausubel et al., *Current Protocols in Molecular Biology*, John Wiley & Sons, Inc. New York (1999), Chapter 7 and Supplement 47; Theophilus et al., "PCR Mutation Detection Protocols," Humana Press, (2002); and Innis et al., *PCR Protocols*, San Diego, Academic Press, Inc. (1990). General nucleic acid hybridization methods are described in Anderson, "Nucleic Acid Hybridization," BIOS Scientific Publishers, 1999. Amplification or hybridization of a plurality of transcribed nucleic acid sequences (e.g., mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

Several markers of interest may be combined into one test for efficient processing of a multiple of samples. In addition, one skilled in the art would recognize the value of testing multiple samples (e.g., at successive time points, etc.) from the same individual. Such testing of serial samples can allow the identification of changes in marker levels over time. Increases or decreases in marker levels, as well as the presence or absence of change in marker levels, can also provide useful information to predict or stratify the risk associated with developing CD in the individual.

A panel consisting of one or more of the markers described above may be constructed to provide relevant information related to the approach of the present invention for predicting or stratifying an individual's risk of developing CD. Such a panel may be constructed using 1, 2, 3, 4, 5, 6, 7, 8, 9, 10, 11, 12, 13, 14, 15, 16, 17, 18, 19, 20, 25, 30, 35, 40, or more individual markers. The analysis of a single marker or subsets of markers can also be carried out by one skilled in the art in various clinical settings. These include, but are not limited to, ambulatory, urgent care, critical care, intensive care, monitoring unit, inpatient, outpatient, physician office, medical clinic, and health screening settings.

The analysis of markers could be carried out in a variety of physical formats as well. For example, the use of microtiter plates or automation could be used to facilitate the processing of large numbers of test samples. Alternatively, single sample formats could be developed to facilitate treatment and diagnosis in a timely fashion.

In one format, the analysis is done by a direct to consumer kit. The consumer purchases a kit from a drug store either under prescription or over the counter and collects a biological sample such as saliva. In certain instances, the sample is sent to a central laboratory and processed. In one optional embodiment, the consumer can register the sample over the internet and receive results via a website. In another embodiment, the kit contains assay reagents or sticks which enable the detection of one or more markers described above.

VI. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

HLA-DQ Genotype Stratifies Patients At Risk For Celiac Disease

A. Methods

Blood samples from 10,191 consecutive subjects who had gastrointestinal symptoms consistent with CD or who were related to patients with CD were analyzed. All uniquely identifying patient information was deleted; only age (without birth date), sex, and laboratory sample number were recorded. The database was thus restricted to preserve the anonymity and confidentiality of the patients' personal medical information. No clinical data were represented in the database, including the reason for the testing.

1. Serologic Testing

Anti-EMA IgA was detected by indirect immunofluorescence using monkey esophagus. Serum samples were incubated with the tissue sections, and bound antibodies were detected using a fluorescein-labeled conjugate. Each tissue section was reviewed by a trained clinical laboratory scientist for antibody detection. A positive result was determined at dilutions of $\geq 1:10$.

Anti-human tissue transglutaminase IgA (tTG) was assayed using an enzyme-linked immunosorbent assay (ELISA) and expressed as U/mL.

Total serum IgA was measured by nephelometry and expressed as mg/dL.

2. Genetic Testing

High-resolution sequence-specific oligonucleotide probe typing of CD-associated HLA-DQ haplotypes was performed on DNA isolated from whole blood. Polymerase chain reaction amplification was carried out with biotinylated primers in two multiplex reactions for the DQA1 and DQB1 locus. The amplified product was then hybridized with 35 DQA1- and 37 DQB1-specific probes, and reactivity patterns were interpreted with LiRAS® software (Innogenetics NV; Gent, Belgium) to identify the alleles present.

Based on the alleles detected, each sample was assigned one of 23 distinct HLA-DQ genotype categories (Table 1). These were organized into four general categories based on the haplotypes detected, as follows:

Category 1. Both the HLA-DQ8 haplotype and one of the two HLA-DQ2 haplotypes were detected;
Category 2. Only HLA-DQ2 haplotypes were detected;
Category 3. Only HLA-DQ8 haplotypes were detected; and
Category 4. Neither haplotype was detected.

TABLE 1

Categorization of Haplotypes by LiRAS Software
DQ2 = A1*05 – B1*0201 or A1*0201 – B1*0202
DQ8 = A1*03 – B1*0302

| DQ2/DQ8 Haplotype Result | Genotype Category | Strand 1 DQA1* | Strand 1 DQB1* | Strand 2 DQA1* | Strand 2 DQB1* |
|---|---|---|---|---|---|
| DQ2 and DQ8 detected | 1A | 0201 | 0202 | 03 | 0302 |
| | 1B | 05 | 0201 | 03 | 0302 |
| DQ2 detected | 2A | 0201 | 0202 | 0201 | 0202 |
| | 2B | 0201 | 0202 | x | y |
| | 2C | 0201 | 0202 | x | 0201 |
| | 2D | 0201 | 0202 | 05 | 0301 |
| | 2E | 05 | 0201 | 05 | 0201 |
| | 2F | 05 | 0201 | x | y |
| | 2G | 0201 | 0202 | 05 | 0303 |
| | 2H | 0201 | 0202 | 05 | 0201 |
| | 2I | 03/05 | 02 | 05 | 02/03* |
| | 2J | 0201 | 0202 | 0201 | 03* |
| DQ8 detected | 3A | 03 | 0302 | c | d |
| | 3B | 03 | 0302 | 03 | 0302 |
| | | 0301/0303 | | 0301/0303 | |
| | 3C | 03 | 0302 | c | 030101, |
| | | 0301/0303 | | | 0602 |
| | | | | | or 0606 |
| DQ2 and DQ8 not detected | 4A | 05 | y | x | y |
| | 4B | 0201 | y | x | y |
| | 4C | 0201 | y | 05 | y |
| | 4D | x | 02 | x | y |
| | 4E | x | y | x | y |
| | 4F | x | y | x | 02 |
| | 4G | 0201 | y | 0201 | y |
| | 4H | 05 | y | 05 | y | x ≠ A1*0201 or *05
y ≠ B1*02 or *0302
c = any DQA1
d ≠ DQB1*0301, *0602 or *0606
03 = any DQA1*03 allele
05 = any DQA1*05 allele
02 = any DQB1*02 allele 3. Stratification Because clinical identifiers had been removed from the laboratory samples, it was necessary to use a laboratory finding to determine if the sample came from a patient with active CD. EMA positivity was used for this purpose because it is highly sensitive (>90%) and extremely specific (>99%) for a diagnosis of CD (Hadithi et al., Ann. Intern. Med., 147(5): 294-302 (2007); Wong et al., Pathology, 35:285-304 (2003); Lewis et al., Aliment. Pharmacol. Ther., 24(1):47-54 (2006)), and it is also highly correlated with villous atrophy (Sollid et al., Nat. Clin. Pract. Gastroenterol. Hepatol., 2(3):140-147 (2005); Wong et al., Pathology, 35:285-304 (2003); Koning, Gastroenterology, 129:1294-1301 (2005)). Although this method could not detect disease in IgA-deficient samples, the number of such samples was recorded.

B. Results

1. Demographic Data

The median age of persons from whom these blood samples were drawn was 41 years (interquartile range, 20 to 58; full range, <1 to 104). Females represented 67.0% of the samples (6829).

2. HLA-DQ Genotype Frequency

Table 2 below presents the HLA-DQ genotype frequency for each of the 23 genotype categories used by Prometheus Laboratories, Inc. Only one of the 10,091 total samples could not be interpreted. The most commonly observed category (4E), accounting for almost one fourth of the total, represented individuals who did not carry even one half of the DQ2 or DQ8 haplotype. The six most frequently occurring categories comprised 72.8% of all samples, whereas the nine least frequently occurring categories accounted for just 4.8% of all samples.

TABLE 2

Occurrence of Each Genotype in Descending Order of Frequency*

| Genotype Category | N | Percent of Total Samples[†] |
|---|---|---|
| 4E | 2385 | 23.41 |
| 2F | 1371 | 13.45 |
| 4A | 1270 | 12.11 |
| 2B | 1005 | 9.86 |
| 3A | 763 | 7.49 |
| 3C | 659 | 6.47 |
| 2I | 369 | 3.62 |
| 2H | 350 | 3.43 |
| 2D | 322 | 3.16 |
| 1B | 298 | 2.92 |
| 4B | 291 | 2.86 |
| 1A | 220 | 2.16 |
| 4H | 203 | 1.99 |
| 2E | 198 | 1.94 |
| 2A | 100 | 0.98 |
| 3B | 95 | 0.93 |
| 2G | 86 | 0.84 |
| 4C | 86 | 0.84 |
| 2J | 67 | 0.66 |
| 4D | 36 | 0.35 |
| 4G | 11 | 0.11 |
| 2C | 4 | 0.04 |
| 4F | 2 | 0.02 |
| Total | 10,190 | 100 |

*One sample could not be interpreted.
[†]Rounded to 2 decimal points.

3. EMA Positivity

Table 3 below presents the rate of EMA positivity for each of the 23 genotype categories. As expected, the DQ2 heterodimer was detected in 90.6% of EMA-positive samples (434 of 479) and was exclusively detected in 77.9% (373 of 479). The DQ8 heterodimer was detected in 20.7% of EMA positive samples overall (99 of 479) and was exclusively detected in 7.9% (38 of 479).

TABLE 3

EMA Positivity by Genotype Category

| Category | N | EMA+ | % EMA+ | 95% CI (Exact) for % EMA+ |
|---|---|---|---|---|
| 1A | 220 | 14 | 6.36 | 3.52-10.45 |
| 1B | 298 | 47 | 15.77 | 11.82-20.42 |
| 2A | 100 | 3 | 3.00 | 0.62-8.52 |
| 2B | 1005 | 5 | 0.50 | 0.16-1.16 |
| 2C | 4 | 0 | 0 | |
| 2D | 322 | 44 | 13.66 | 10.11-17.91 |
| 2E | 198 | 53 | 26.77 | 20.74-33.51 |
| 2F | 1371 | 134 | 9.77 | 8.25-11.47 |
| 2G | 86 | 5 | 5.81 | 1.91-13.05 |
| 2H | 350 | 102 | 29.14 | 24.43-34.21 |
| 2I | 369 | 27 | 7.32 | 4.88-10.47 |
| 2J | 67 | 0 | 0 | |
| 3A | 763 | 19 | 2.49 | 1.51-3.86 |
| 3B | 95 | 8 | 8.42 | 3.71-15.92 |
| 3C | 659 | 11 | 1.67 | 0.84-2.97 |
| 4A | 1270 | 2 | 0.16 | 0.02-0.57 |
| 4B | 291 | 1 | 0.34 | 0.01-1.90 |
| 4C | 86 | 0 | 0 | |
| 4D | 36 | 2 | 5.56 | 0.68-18.66 |
| 4E | 2385 | 2 | 0.08 | 0.01-0.30 |
| 4F | 2 | 0 | 0 | |
| 4G | 11 | 0 | 0 | |
| 4H | 203 | 0 | 0 | |
| Total | 10,190 | 479 | 4.70 | 4.30-5.13 |

Because many of the genotype categories comprised a very small percentage of the total sample, and to facilitate interpretation and reporting of the results, the 23 genotype categories were condensed into eight genotype groups. Table 4 below compares the percentage of samples that were EMA positive for each of these groups.

TABLE 4

EMA Positivity by Genotype Groups (Descending Order)

| Genotype | Constituent Categories | N | EMA+ | % EMA+ | 95% CI |
|---|---|---|---|---|---|
| DQ2 homozygous | 2E, 2H | 548 | 155 | 28.28 | 24.55-32.26 |
| DQ2.2/other high-risk alleles | 2D | 322 | 44 | 13.66 | 10.11-17.91 |
| DQ2/DQ8 | 1A, 1B | 518 | 61 | 11.78 | 9.13-14.87 |
| DQ2.5 heterozygous | 2F, 2G, 2I | 1826 | 166 | 9.09 | 7.81-10.50 |
| DQ8 homozygous | 3B | 95 | 8 | 8.42 | 3.71-15.92 |
| DQ8 heterozygous | 3A, 3C | 1422 | 30 | 2.11 | 1.43-3.00 |
| DQ2.2/other low-risk alleles | 2A, 2B, 2C, 2J | 1176 | 8 | 0.68 | 0.29-1.34 |
| DQ2/-DQ8 | 4A thru 4H | 4283 | 7 | 0.16 | 0.07-0.34 |
| Total | All | 10,190 | 479 | 4.70 | 4.30-5.13 |

DQ2.5 heterozygous samples were analyzed as a single group, whereas DQ2.2 samples were divided into two groups, "other high-risk alleles" and "other low-risk alleles." This was done because the DQ2.2 haplotype itself, whether heterozygous or homozygous, was not independently associated with an increased risk for EMA positivity. However, when it was paired with the DQA1*05-DQB1*03 haplotype, the resulting heterodimers were associated with a greater rate of EMA positivity (13.66%) than that found with the DQ2.5 heterozygotes (9.09%).

An odds ratio analysis was performed for DQ2 and DQ8 genotypes. The odds ratio for EMA positivity for DQ2 homozygous samples as compared with DQ2.5 heterozygous samples was 3.94 (95% confidence interval [CI], 3.09 to 5.04; P<0.0001, Fishers exact test). Similarly, the odds ratio for EMA positivity for DQ8 homozygous samples as compared with DQ8 heterozygous samples was 4.27 (95% CI, 1.900 to 9.585; P=0.0018, Fishers exact test).

To determine the statistical significance of the difference between the rates of EMA positivity for the groups with the most similar rates, a nearest neighbor analysis was performed on three pairs of genotype groups. The first pair was the samples with the lowest occurrence of EMA positivity, DQ2/DQ8 and DQ2.2/other low-risk alleles. Their EMA positivity rates—0.16% and 0.68%, respectively—were found to be significantly different (P=0.0068). However, the rate of EMA positivity in the DQ2/DQ8 group (11.78%) was not significantly different from that of the DQ2.2/other high-risk alleles group (13.66%; P=0.453). Similarly, there was no significant difference between the EMA positivity rates for the DQ8 homozygous (8.42%) and the DQ2.5 heterozygous (9.09%) groups (P=0.999).

The EMA positivity rate among females was 4.50% (307 of 6829 samples), and among males, it was 5.12% (172 of 3362 samples).

A total of 75 samples (0.74%) were IgA deficient (defined as <6.7 mg/dL), approximately four times the population prevalence of 0.2%. Among the samples that were IgA deficient, 13 of 75 (17.33%) were DQ2 homozygous, compared with 4.61% of the remaining samples (466 of 10,115).

In 19 cases of EMA positivity, the tTG was negative ($\leq 4.0$ U/mL). Conversely, in 24 cases of tTG positivity (>4.0 U/mL), the EMA was negative. Expressed alternatively, of the 479 samples that were EMA positive, 19 of 479, or 4.0%, were tTG negative, whereas of the 484 samples that were tTG positive, 24 of 484, or 5.0%, were EMA negative. All of the cases in which tTG was positive but EMA was negative occurred in samples for which the total tTG was $\leq 10$ U/mL.

C. Discussion

1. Major Discoveries

This is the largest and most detailed database of HLA genetics reported from a US population at risk for CD. DQ2 homozygous status dramatically elevated the risk for CD, as estimated by the rate of EMA positivity, in comparison with the sample population as a whole as well as with other DQ genotypes. As previously reported, the absence of DQ2 or DQ8 haplotypes essentially ruled out CD. The stratified risk among the remaining genotype groups ranged from 2.11% for DQ8 heterozygotes to 28.28% for DQ2 homozygotes. There was an orderly progression of risk based on the genotype groups shown in Table 4, which can be further condensed into five general relative-risk levels: (1) extremely high: DQ2 homozygous (~30); (2) very high: DQ2.2/DR5 and DQ2/DQ8 (~12 to 14); (3) high: DQ2.5 heterozygous and DQ8 homozygous (~9); (4) elevated: DQ8 heterozygous (~2); and (5) diminished to none: DQ2.2 heterozygous and -DQ2/-DQ8.

The greater binding affinity of the DQ2 heterodimer for gluten peptide fragments over that of the DQ8 heterodimer (Kim et al., *Proc. Natl. Acad. Sci. USA*, 101:4175-4179 (2004); Qiao et al., *J. Immunol.*, 173:1757-1762 (2004); Sollid et al., *Clin. Gastroenterol. Hepatol.*, 3:843-851 (2005)) is clearly reflected in the much greater risk of EMA positivity associated with DQ2 heterodimers than DQ8 heterodimers. For each allelic combination yielding a DQ8 heterodimer, there appears to be a slightly greater than 2% risk of EMA positivity, versus a risk of approximately 8% to 9% for each allelic combination yielding a DQ2 heterodimer.

In addition, the relative risk for EMA positivity of DQ8 homozygous versus DQ8 heterozygous samples was similar to that of homozygous DQ2 versus heterozygous DQ2 samples. This was documented by the odds ratio of approximately 4 for both of these comparisons. This ratio is consistent with the hypothesized role played by the DQ2 and DQ8 heterodimers in increasing disease risk, because homozygotes can form four DQ2 or DQ8 heterodimers (two cis and two trans), whereas heterozygotes can only form one (one cis). This relative risk also makes theoretical sense, based on the hypothesis that the binding of pathogenic peptide fragments by these heterodimers in a necessary, but not sufficient, component of the pathophysiology of CD. This provides the pathophysiologic rationale for why risk stratification based on HLA-DQ genotype appears to work so well.

These data demonstrate that knowing the HLA-DQ genotype, and therefore the types and proportion of heterodimers resulting from that genotype, seems to be a very powerful tool for stratifying disease risk. If the assay had identified only the presence or absence of the HLA-DQ2 or HLA-DQ8 haplotypes, the risk stratification of these samples would have been limited to showing a CD-associated haplotype detected in 5,907 samples (58.0% of the total), among which 8.0% were EMA positive, and, among the remaining 4,283 samples, a finding of 7 EMA positive samples (0.16%).

2. Implications for the Role of HLA DQ Testing in CD Screening. The most important population that could benefit from this approach to risk stratification is the population of individuals with a positive family history of CD. In particular, a parent with CD could obtain an estimate of risk for each newborn. As noted previously (Fasano, Gut, 52:168-169 (2003); Liu et al., Gastroenterology, 128(4 suppl 1):S33-S37 (2005); Bourgey et al., Gut, 56:1054-1059 (2007)), a negative result for DQ2 and DQ8 effectively rules out CD for life. Because our samples also included adults and children at risk for CD on the basis of clinical symptoms—a population that has a lower prevalence of CD than family members—it is likely that the percentage of individuals in the "virtually no risk" category is less than the 42.0% found in this set of samples.

However, the additional risk stratification presented here provides much more useful information for these families. Those with DQ2.2/not DQA105*, which in our sample represented 11.5% of the population, would also have a known negligible risk for CD (0.68%, or less than the population at large). Individuals who are DQ8 heterozygous, which in our sample represented 14.0% of the population, would have only slightly more than twice the risk of the general population, at 2.11%. Thus, only 32.5% of the population at risk for CD would be informed that they had a substantially elevated risk of developing the illness. Only 5.4% of the total sample would be in the highest-risk group, while the remaining 28.1% would have a risk between approximately 8% and 14% (1 in 12 to 1 in 7).

Although genetic counseling is advisable in the context of genetic testing for any hereditary disease, and some individuals may choose to forego it, for many the additional information provided by genetic risk assessment can provide substantial relief if the results are favorable, and a critical piece of information to aid them in developing with their physician a plan for follow up evaluation.

Diagnosis. A second group of patients who could potentially benefit from more detailed risk stratification are those presenting symptoms consistent with CD. Genetic testing is not typically recommended to these patients because of the general consensus that, in routine situations, serologic screening is much more sensitive and nearly as specific for CD as genetic testing. A recent study comparing serologic testing to genetic testing and to the combination of both showed that adding genetic testing to serologic testing did not increase the diagnostic accuracy over serologic data alone (Hadithi et al., Ann. Intern. Med., 147(5):294-302 (2007)).

However, there are situations where genetic testing can be useful. Patients who are IgA deficient, for example, are at risk of yielding false-negative serologic test results. The fact that these patients are already in a higher-risk category for CD suggests that they have a higher rate of higher-risk genotypes than the general population, which was in fact shown here. Therefore, genetic testing could indicate the need for further evaluation for CD in those with a high-risk genotype, while suggesting that those without such a genotype are unlikely to have CD.

Patients already on a gluten-free diet, which many adopt for a variety of reasons, are not good candidates for serologic testing. Genetic testing, on the other hand, could identify the one third of patients who are at markedly elevated risk of CD and could provide those individuals with a more evidence-based rationale for their dietary restrictions. Genetic testing could also provide other patients with a strong justification for not needing gluten restriction.

Despite the excellent sensitivity and specificity of serologic testing for CD, and given the status of histology as the gold standard for diagnosis, there remain certain cases of equivocal diagnosis based on serologic and histologic findings. In such cases, genetic testing could assist the clinician in making the diagnosis by providing information regarding the likelihood of CD in that particular patient.

Finally, some patients with positive serologic results do not wish to undergo endoscopic evaluation, and some parents do not wish to subject their child to the procedure. It is not unreasonable to suggest that, given the sensitivity and specificity of current serologic testing, if positive serologic results are combined with a determination of a higher-risk genotype in the presence of symptoms consistent with CD, the chance that CD is present approaches certainty. In such patients, institution of a gluten-free diet should lead to remission of symptoms, and only nonresponse to the diet would suggest the need for further diagnostic work-up. Conversely, if the genotype is consistent with less than a 1% risk for CD, it alerts the clinician that the likelihood of a false-positive screening test is quite high. In those cases, the evaluation should be directed to ruling in alternative diagnoses consistent with the presenting symptoms.

Research. Risk stratification could also play a role in celiac disease research by identifying patient groups at elevated risk for the development of celiac disease prior to the development of clinical symptoms. Such individuals would be ideal research subjects to test a variety of preventive interventions, such as digestive enzyme supplementation, pharmacologic strategies targeting CD risk heterodimers, or others that have been suggested (Sollid et al., Nat. Clin. Pract. Gastroenterol. Hepatol., 2(3):140-147 (2005)). From a statistical perspective, such an enriched population could allow for the design of studies involving fewer subjects and shorter durations of follow up.

3. Comparison with Existing U.S. Data

The most comprehensive study of Celiac disease epidemiology reported from the United States is that of Fasano and colleagues from 2003 (Fasano, Gut, 52:168-169 (2003)). This pivotal multicenter epidemiologic study involved 13,145 subjects, all of whom were serologically screened for EMA. In those who tested positive for EMA, anti-tTG antibodies were measured and DQ2/DQ8 haplotypes were determined. At-risk subjects (n=9019) were either first- or second-degree relatives of biopsy-proven CD patients or were patients with gastrointestinal symptoms or other disorders suggestive of CD; the not-at-risk subjects (n=4126) comprised blood donors, school children, and adults seen for routine checkups. The prevalence of EMA positivity in this not-at-risk subset was 1:133. This compared with a prevalence of 1:22 in first-degree relatives, 1:39 in second-degree relatives, and 1:56 in symptomatic patients. Intestinal biopsy was recommended (but not always performed) on EMA-positive patients. In all of those in whom it was done (116 of 350, or 33%), the histology was compatible with a diagnosis of CD.

These data are supportive of the usefulness of EMA positivity as a proxy for the diagnosis of CD. The percentage of EMA-positive first-degree relatives (4.65%) was also similar to our overall positivity rate of 4.70%, as was the EMA positivity rate in symptomatic children (4.00%). Because we cannot know what percentage of the samples in our database came from first-degree relatives as opposed to symptomatic adults or children, it is difficult to make any further comparisons.

4. Comparison with Existing European Data

Substantially more data on the relationship of DQ haplotype to CD is available in the European literature, and it is also more varied. Based on a systematic literature review, the CD prevalence in Western Europe, ~1%, is similar to that reported in the United States. (Dubé et al., *Gastroenterology*, 128(4 suppl 1):S57-S67 (2005)). Similarly, genetic studies of first-degree relatives of CD probands have also found that those with serologically and histologically confirmed disease are almost all positive for DQ2 and/or DQ8 haplotypes (Bourgey et al., *Gut*, 56:1054-1059 (2007); Karell et al., *Hum. Immunol.*, 64:469-477 (2003); Karinen et al., *Scand. J. Gastroenterol.*, 41:1299-1304 (2006)).

5. Secondary Observations

The issue of whether or not risk for CD is equal among the sexes or more prevalent in females is not known. In this set of blood samples, approximately two-thirds were from females and one-third were from males. Thus, even though the number of EMA-positive samples from females was roughly twice the number from males, this is proportional to the number tested. The rate of EMA positivity in men was actually 10% higher (5.12 versus 4.7). Again, lacking clinical information, these data must be interpreted cautiously. Nonetheless, they seem to suggest that the prevalence of disease is approximately the same among males and females, but that females are tested more frequently.

Also debatable is the age at which serologic testing can be considered a reliable marker of active CD. In this data set, there were no EMA-positive samples in persons <1 year of age (0/17), and only 1.85% were EMA positive in those between ages 1 and 2 (3 of 162). Individuals between the age of 2 and 3 had the same EMA positivity rate as those between the age of 3 and 4 (4.08% and 4.03%, respectively), and this was approximately the same as the overall EMA positivity rate of 4.70%. These data are consistent with the general consensus that serologic testing in children under 2 years of age is not indicated, but that somewhere between 2 and 3 years of age the reliability of serologic testing begins to approach that for the rest of the population.

Careful consideration of the observed risk for each of the genotype categories, however, suggests that there must be other heterodimers that confer risk besides the DQ2 and DQ8 heterodimers, as the latter seem to not account for the total risk of each of the categories in which they are found. For example, genotype 1A comprises a DQ2.2 haplotype and a DQ8 haplotype. The heterodimers resulting from this combination would be 25% DQ8, 25% DQA1*0201-DQB1*0202, 25% DQA1*02-DQB1*03, and 25% DQA1*02-DQB1*03. However, the total risk for category 1A was 6.36% (Table 3), which is greater than the sum of the observed 2.11% risk for the DQ8 heterozygous category (also yielding 25% DQ8 heterodimers, Table 4) and the 0.68% observed risk for the DQ2.2/other low-risk alleles (also yielding 25% DQA1*0201-DQB1*0202 heterodimers, Table 4). Therefore, the risk not attributable to those heterodimers is 6.36%− (2.11%+0.68%)=3.57%. This remaining risk may thus be attributed to these other heterodimers, both of which represent combinations of *02 and *03 alleles. In the absence of any evidence that it matters which is the alpha chain and which the beta, the risk may be assumed to be equally divided between these two heterodimers, approximately 1.78% for each.

Category 1B, comprising the haplotypes DQ2.5 and a DQ8, may be similarly considered. The heterodimers resulting from this pairing would be 25% DQ2, 25% DQ8, 25% DQA1*05-DQB1*03, and 25% DQA1*03-DQB1*02. The total risk for this category was 15.77% (Table 3). Because the risk for category 2E was 9.09% (25% DQ2 heterodimers) and that for DQ8 heterozygotes (Table 4) was 2.11%, again there is a remaining risk of 15.77%−(9.09%+2.11%)=4.57%. If the estimate for the DQA1*03-DQB1*02 heterodimer calculated in the preceding paragraph is applied here, the remaining risk attributable to the fourth heterodimer, DQA1*05-DQB1*03, would be 4.57%−1.78%=2.79%.

There is one more category that is important to consider in this regard, and that is category 2D, comprising a DQ2.2 haplotype and a DQA1*05-DQB1*03 haplotype. The heterodimers yielded by this genotype are 25% DQ2, 25% DQA1*0201-DQB1*0202, 25% DQA1*05-DQB1*03, and 25% DQA1*02-DQB1*03. The observed risk attributable to DQ2 is 9.09%, and the calculated risk attributable to DQA1*05-DQB1*03 is 2.79%; observed risk attributable to DQA1*03-DQB1*02 is 1.78%, and to DQA1*0201-DQB1*0202 is 0.68%. The sum of these risks is 14.34%, which is certainly close to the observed risk for category 2D of 13.66%.

A total of 15 samples were EMA positive among the 5359 samples with genotypes incompatible with the formation of a DQ2 or DQ8 heterodimer (0.22%, categories 2A, 2B, 2C, 2J, and all 4s). However, as illustrated above, it appears likely that a small but distinct percentage of EMA-positive samples that were observed in genotype categories that do yield one or more DQ2 or DQ8 heterodimers may be attributable to other heterodimers also formed in individuals of those genotypes. In other words, even though individuals with those genotypes do form DQ2 and/or DQ8 heterodimers, it appears that these DQ2 and DQ8 heterodimers cannot account for all of the risk of EMA positivity in those samples.

This observation may help to solve the puzzle of the apparently large number (61 of 1008, or 6.05%) of European CD patients who were identified as not carrying the DQ2 or DQ8 heterodimer (The European Genetics Cluster on Celiac Disease, Karell et al., *Hum. Immunol.*, 64:469-477 (2003)). In that data set, 57 of those 61 cases were positive for carrying one of the two alleles necessary for the formation of a DQ2 or DQ8 haplotype. However, there is no such entity as half of a heterodimer, so it is not entirely clear why having only the α or only the β chain of a risk heterodimer would confer actual risk of disease. If, however, it is true that the non-DQ2, non-DQ8 heterodimers identified above do confer some risk for CD, then the data from the European study make more sense. Table 2 of that seminal article presented the observed alleles in each of the 61 patients negative for DQ2 and DQ8. Of these, 11 were DQ2.2 homozygous (a 3.0% risk in the data presented here, category 2A), 11 were capable of forming an DQA1*02-DQB1*03 heterodimer (1.78% risk), 16 had a DQA1*05-DQB1*03 haplotype (resulting heterodimer, 2.79% risk), and 14 were capable of forming a DQA1*02-DQB1*05 heterodimer (none noted in this data set, but it is plausible that even though the *02 and *05 chains are reversed, the heterodimer might still confer some risk for CD). Thus, most of these cases appear to have been associated with the presence of one of several heterodimers that, according to these data, appear to also convey some small risk of CD.

D. Conclusions

It has been discovered that HLA-DQ genotype can effectively stratify patients at risk for CD (e.g., relatives of patients with biopsy-proven disease) into clinically meaningful risk groups. Such stratification can provide benefits to family members of CD patients, to a subset of patients who are being evaluated clinically for CD, and to researchers, who could utilize this strategy to establish inclusion criteria for participation in research studies investigating potential preventive interventions.

This analysis of 10,191 samples also provides additional confirmatory evidence that binding of gluten-derived peptide fragments by particular DQ heterodimers is a necessary, but not sufficient cause of CD. It extends existing data to suggest a quantitative relationship between the type and proportion of DQ heterodimers and the risk of CD, and it indicates specific heterodimers other than DQ2 or DQ8 that may be responsible for a small percentage of cases. Further exploration of the value of DQ genetic-based risk stratification for the screening and diagnosis of CD, as well as for research into preventive interventions, is clearly warranted.

Example 2

Specific HLA-DQ Genotypes Are Associated with Elevated Anti-CBir1 Antibody Levels This example illustrates that serum immune responses to anti-CBir1 flagellin antibodies correlates with HLA-DQA1*05-DQB1*0201 (DQ2.5) and DQA1*03-DQB1*0302 (DQ8) genotypes in a large group of U.S. patients at risk for celiac disease (n=5406) who are EMA positive.

Celiac disease (CD) is caused by an inappropriate immune response to wheat gluten proteins, and similar proteins in rye and barley, in genetically susceptible individuals. The prevalence is estimated to be 1% of the U.S. population, similar to that of the European Union. Important genetic predisposing factors are HLA-DQ2 and HLA-DQ8, which are necessary but not sufficient for the development of CD, as they are present in up to 30% of healthy individuals. Thus, many patients possess both risk factors (genes and gluten ingestion) and never develop CD. As in inflammatory bowel disease, an overly aggressive immune response to resident luminal bacterial constituents, such as flagellin, may contribute to the intestinal inflammation seen in CD.

In this example, the aim was to test serum immune responses in U.S. patients at risk for CD to CBir-1 and to stratify risk for CBir-1 positivity by HLA haplotype. Methods: EMA IgA was detected by indirect immunofluorescence. ELISA was performed using the $NH_2$-terminal fragment of CBir-1 (147 amino acids). High-resolution, sequence-specific oligonucleotide probe typing of CD-associated HLA-DQ haplotypes was performed. Amplified PCR products from whole blood were hybridized with 35 DQA1- and 37 DQB1-specific probes. Reactivity patterns were interpreted with LiRAS® software (Innogenetics NV, Belgium). Samples were stratified into 23 distinct HLA-DQ genotype categories (Prometheus Laboratories Inc., San Diego).

Results: 5406 sera were analyzed between October 2006 and June 2008. 105 patients were EMA positive (2%). Almost half of the EMA positives (45%) had elevated anti-CBir-1 antibody levels compared to EMA negatives (Chi-square p=0.03; Wilcoxon rank sum test p=0.007). HLA-DQ2.5 (DQA1*05-DQB1*0201) and DQ8 (DQA1*03-DQB1*0302), but not DQ2.2 (DQA1*0201-DQB1*0202), correlated with elevated anti-CBir-1 antibody levels (Chi-square p<0.01 and p<0.05, respectively).

Conclusions: EMA positivity in U.S. patients at risk for CD is associated with an aberrant immunologic response to intestinal commensal bacteria, which may contribute to bowel inflammation via both the innate and adaptive immune system. Elevation of anti-CBir-1 flagellin antibody levels correlates with possession of HLA haplotypes DQ2.5 and DQ8. Flagellin is the ligand for TLR5, activating NFkB which is required for the transcriptional induction of proinflammatory cytokines. Phenotypic associations with these serologic patterns are needed to determine the frequency of CD complications, such as lymphocytic colitis, enteropathy-associated T-cell lymphoma, and refractory sprue, and their correspondence with active or remission disease states while on the gluten-free diet.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Genbank Accession Nos., are incorporated herein by reference for all purposes.

INFORMAL SEQUENCE LISTING

SEQ ID NO:1

Genbank Accession No. AAT06254

CBir-1 flagellin [uncultured bacterium], protein 1 mvvqhnlqam nsnrmlgitq ktaskstekl ssgyainraa dnaaglaise kmrkqirglt 61 qastnaedgi ssvqtaegal tevhdmlqrm nelaiqaang tnseddrsyi qdeidqltqe 121 idrvaettkf netyllkgdt knvdamdyty sykavttntv arasvlaaen tatgmsysis 181 faansgkvta adsnnlakai rdqgftitts tqngkvvygl elngsdakan ytvstvsmea 241 gtfkilnsnk qvvasvtist tasfkkvsgm sqivtaysys aayatgdvys lydadgnais 301 ankldkyfta ggateaggia ttlsansgvp kvydvlgkev saysiastiv tavkdktaal 361 kmnfhvgadg tdnnkikini eamtakslgv nglkvsgssg tnatnaieii agaikkvstq 421 rsalgavqnr lehtinnldn iventtaaes girdtdmate mvkysnanil sqaggsmlaq 481 snqsnqgvlq llq

What is claimed is:

1. A method for aiding in the prediction of whether an individual having a relative with celiac disease (CD) is at risk of developing CD, the method comprising:
    (a) contacting a sample from the individual with a CBir1 flagellin antigen under conditions suitable to form a complex of the CBir1 flagellin antigen and an anti-CBir1 flagellin antibody, wherein the CBir1 flagellin antigen comprises the amino terminal conserved region (amino acid residues 1-147) of the sequence set forth in SEQ ID NO:1;
    (b) contacting the complex with a labeled antibody to form a labeled complex;
    (c) detecting the level of the labeled complex with a detection device, thereby determining a level of anti-CBir1 flagellin antibodies in the sample; and
    (d) associating an elevated level of anti-CBir1 flagellin antibodies in the sample relative to a control with a high risk of developing CD,
    thereby aiding in the prediction of whether an individual having a relative with CD is at risk of developing CD.

2. The method of claim 1, wherein the sample is selected from the group consisting of whole blood, serum, plasma, urine, feces, and a tissue biopsy.

3. The method of claim 1, wherein the presence of an elevated level of anti-CBir1 flagellin antibodies is associated with an about 9-fold increased risk of developing CD.

4. The method of claim 1, wherein the control is negative for anti-endomysial antibodies.

5. The method of claim 1, wherein the individual has an HLA-DQ2.5 or HLA-DQ8 genotype.

6. The method of claim 1, wherein the level of anti-CBir1 flagellin antibodies is determined using an immunoassay or immunohistochemical assay.

7. The method of claim 1, wherein the immunoassay is an enzyme-linked immunosorbent assay (ELISA).

8. The method of claim 1, wherein the method further comprises sending the results from the prediction to a clinician.

9. A method for aiding in the prediction of whether an individual positive for anti-endomysial antibodies (EMA) is at risk of developing celiac disease (CD), the method comprising:
    (a) contacting a sample from the individual with a CBir1 flagellin antigen under conditions suitable to form a complex of the CBir1 flagellin antigen and an anti-CBir1 flagellin antibody, wherein the CBir1 flagellin antigen comprises the amino terminal conserved region (amino acid residues 1-147) of the sequence set forth in SEQ ID NO:1;
    (b) contacting the complex with a labeled antibody to form a labeled complex;
    (c) detecting the level of the labeled complex with a detection device, thereby determining a level of anti-CBir1 flagellin antibodies in the sample; and
    (d) associating an elevated level of anti-CBir1 flagellin antibodies in the sample relative to a control with a high risk of developing CD, thereby aiding in the prediction of whether an individual positive for anti-EMA is at risk of developing CD.

10. The method of claim 9, wherein the sample is selected from the group consisting of whole blood, serum, plasma, urine, feces, and a tissue biopsy.

11. The method of claim 9, wherein the presence of an elevated level of anti-CBir1 flagellin antibodies is associated with an about 9-fold increased risk of developing CD.

12. The method of claim 9, wherein the control is negative for anti-endomysial antibodies.

13. The method of claim 9, wherein the individual has an HLA-DQ2.5 or HLA-DQ8 genotype.

14. The method of claim 9, wherein the level of anti-CBir1 flagellin antibodies is determined using an immunoassay or immunohistochemical assay.

15. The method of claim 14, wherein the immunoassay is an enzyme-linked immunosorbent assay (ELISA).

16. The method of claim 9, wherein the method further comprises sending the results from the prediction to a clinician.

17. The method of claim 1, wherein the CBir1 flagellin antigen further comprises a six histidine tag.

18. The method of claim 1, wherein the labeled antibody comprises a reporter group.

19. The method of claim 18, wherein the reporter group comprises a fluorescent group, a radioactive group, a luminescent group, an enzyme, biotin, or a dye.

20. The method of claim 1, wherein the detection device comprises a plate reader, a spectrophotometer, or a fluorimeter.

21. The method of claim 9, wherein the CBir1 flagellin antigen further comprises a six histidine tag.

22. The method of claim 9, wherein the labeled antibody comprises a reporter group.

23. The method of claim 22, wherein the reporter group comprises a fluorescent group, a radioactive group, a luminescent group, an enzyme, biotin, or a dye.

24. The method of claim 9, wherein the detection device comprises a plate reader, a spectrophotometer, or a fluorimeter.

* * * * *